United States Patent
Nishino

(10) Patent No.: US 10,071,481 B2
(45) Date of Patent: Sep. 11, 2018

(54) SAFETY SYSTEM FOR INDUSTRIAL ROBOTS

(71) Applicant: DENSO WAVE INCORPORATED, Chita-gun, Aichi-pref. (JP)

(72) Inventor: Hideyuki Nishino, Chita-gun (JP)

(73) Assignee: DENSO WAVE INCORPORATED, Aichi-Pref. (JP)

(*) Notice: Subject to any disclaimer, the term of this patent is extended or adjusted under 35 U.S.C. 154(b) by 0 days.

(21) Appl. No.: 15/364,807

(22) Filed: Nov. 30, 2016

(65) Prior Publication Data

US 2017/0197313 A1    Jul. 13, 2017

(30) Foreign Application Priority Data

Nov. 30, 2015 (JP) ................................ 2015-233298

(51) Int. Cl.
| | |
|---|---|
| *G08B 1/08* | (2006.01) |
| *B25J 9/16* | (2006.01) |
| *G06F 3/147* | (2006.01) |
| *A61B 5/0205* | (2006.01) |
| *A61B 5/024* | (2006.01) |

(52) U.S. Cl.
CPC ......... *B25J 9/1676* (2013.01); *A61B 5/02055* (2013.01); *G06F 3/147* (2013.01); *A61B 5/024* (2013.01); *G05B 2219/39082* (2013.01); *G05B 2219/40202* (2013.01); *Y10S 901/46* (2013.01); *Y10S 901/49* (2013.01)

(58) Field of Classification Search
CPC ....................................................... B25J 9/1676
USPC ..................................................... 340/539.11
See application file for complete search history.

(56) References Cited

U.S. PATENT DOCUMENTS

| | | | |
|---|---|---|---|
| 9,387,587 B2* | 7/2016 | Som ........................ | B25J 9/1656 |
| 9,649,766 B2* | 5/2017 | Stubbs .................... | B25J 9/1666 |
| 9,694,497 B2* | 7/2017 | Burmeister ............ | B25J 9/1676 |
| 2004/0236469 A1* | 11/2004 | Moridaira .............. | B25J 9/1674 700/245 |
| 2005/0280544 A1* | 12/2005 | Mishelevich ........... | A24F 47/00 340/573.1 |
| 2008/0161970 A1* | 7/2008 | Adachi ................... | B25J 9/0003 700/253 |
| 2009/0128079 A1* | 5/2009 | Sjoberg .................... | B25J 13/06 318/568.13 |
| 2009/0222134 A1* | 9/2009 | Franke ............... | G05B 19/4061 700/251 |

(Continued)

*Primary Examiner* — Santiago Garcia
(74) *Attorney, Agent, or Firm* — Oliff PLC

(57) ABSTRACT

A system to secure people's safety in places such as a factory wherein people and industrial robot collaborate with each other in a state that a physical fence surrounding the preferred industrial robot's working region is excluded. The system is capable of acquiring respective distances between robot and a plurality of people. Furthermore, a critical distance of each person is set on the basis of at least one of personal information that each person individually has and environment information to be set depending on the robot's setting environment. A mounted-type monitor is respectively mounted on the plurality of people and is capable of displaying information within a view of each person, and a control unit is capable of controlling display content thereon. According to the display control, when a distance between robot and each person becomes less than a critical distance, the distance state is displayed on the mounted-type monitor.

13 Claims, 15 Drawing Sheets

(56) References Cited

U.S. PATENT DOCUMENTS

| | | | |
|---|---|---|---|
| 2011/0135429 A1* | 6/2011 | Machida | B23P 21/00 414/222.13 |
| 2011/0320038 A1* | 12/2011 | Motoki | B25J 19/0008 700/245 |
| 2012/0184367 A1* | 7/2012 | Parrott | G06F 1/163 463/31 |
| 2012/0204307 A1* | 8/2012 | De Mattei | A41D 1/002 2/69 |
| 2012/0290132 A1* | 11/2012 | Kokubo | B25J 9/1666 700/255 |
| 2013/0338829 A1* | 12/2013 | Schlaich | B25J 9/1676 700/253 |
| 2014/0018958 A1* | 1/2014 | Ueno | B25J 9/1674 700/255 |
| 2014/0067121 A1* | 3/2014 | Brooks | B25J 9/1676 700/255 |
| 2014/0365242 A1* | 12/2014 | Neff | G06F 19/322 705/3 |
| 2015/0145985 A1* | 5/2015 | Gourlay | G06T 17/00 348/135 |
| 2015/0209961 A1* | 7/2015 | Komatsu | B25J 9/1676 700/255 |
| 2015/0332463 A1* | 11/2015 | Galera | G06K 9/00771 382/103 |
| 2016/0271800 A1* | 9/2016 | Stubbs | B25J 9/1666 |
| 2016/0274586 A1* | 9/2016 | Stubbs | G06K 7/10366 |
| 2016/0346935 A1* | 12/2016 | Nakayama | B25J 13/085 |
| 2017/0028565 A1* | 2/2017 | Matsudaira | B25J 9/1674 |
| 2017/0095932 A1* | 4/2017 | Murakami | B25J 9/1612 |
| 2017/0143429 A1* | 5/2017 | Richmond | A61B 34/20 |
| 2017/0157783 A1* | 6/2017 | Ogawa | B25J 19/06 |

* cited by examiner

FIG.3

| INFORMATION TYPE | | | INDIVIDUAL CONDITIONS | INDIVIDUAL COEFFICIENT $\alpha i$ | |
|---|---|---|---|---|---|
| INDIVIDUAL INFORMATION | BASIC INFORMATION | GENDER | MAN | $\alpha 1$ | 0 |
| | | | WOMAN | | 0.2 |
| | | AGE | IN HIS OR HER FIFTIES | $\alpha 2$ | 0 |
| | | | IN HIS OR HER FORTIES | | 0.1 |
| | | | IN HIS OR HER THIRTIES | | 0.2 |
| | | | IN HIS OR HER TWENTIES | | 0.3 |
| | | WORKING EXPERIENCE | MORE THAN 20 YEARS | $\alpha 3$ | 0 |
| | | | 20~11 YEARS | | 0.1 |
| | | | 10~5 YEARS | | 0.2 |
| | | | LESS THAN 5 YEARS | | 0.3 |
| | BIOLOGICAL INFORMATION | BODY TEMPERATURE | NORMAL TEMPERATURE | $\alpha 4$ | 0 |
| | | | EQUAL TO OR MORE THAN "NORMAL TEMPERATURE + 0.5 °C" | | 0.2 |
| | | | EQUAL TO OR LESS THAN "NORMAL TEMPERATURE - 0.5 °C" | | 0.2 |
| | | PULSE | UNDER NORMAL CONDITIONS | $\alpha 5$ | 0 |
| | | | INCREASE WHEN STARING WORK | | 0.1 |
| | | | DECREASE WHEN STARING WORK | | 0.1 |
| ENVIRONMENT INFORMATION | | TIME PERIOD | AFTER A MEAL TIME AND BREAK | $\alpha 6$ | 0.1 |
| | | | DISASTER OCCURRENCE TIME ± WITHIN ONE HOUR | | 0.2 |
| | | PLACE | PLACE AROUND WHERE DISASTER OCCURRED | $\alpha 7$ | 0.2 |

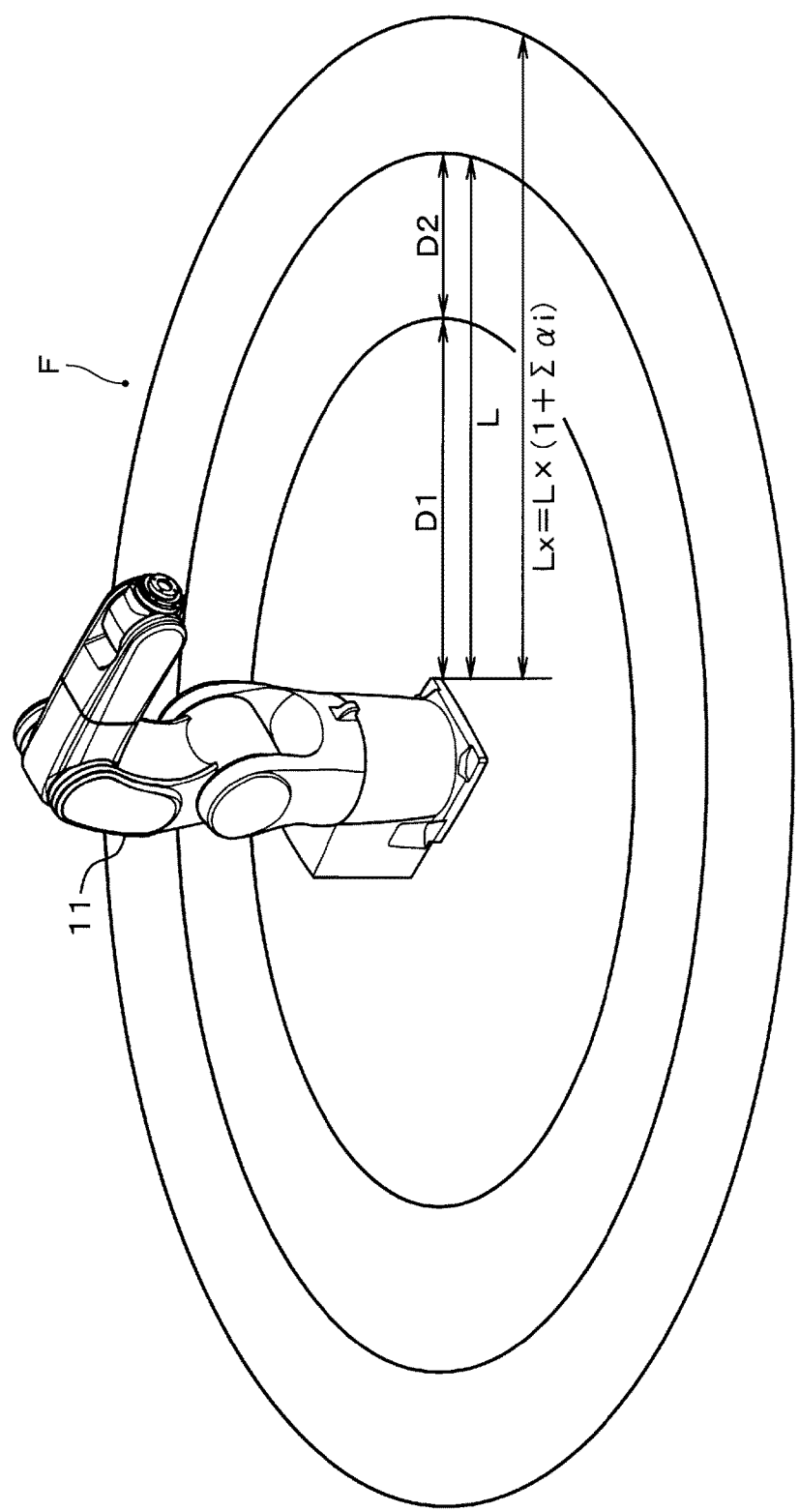

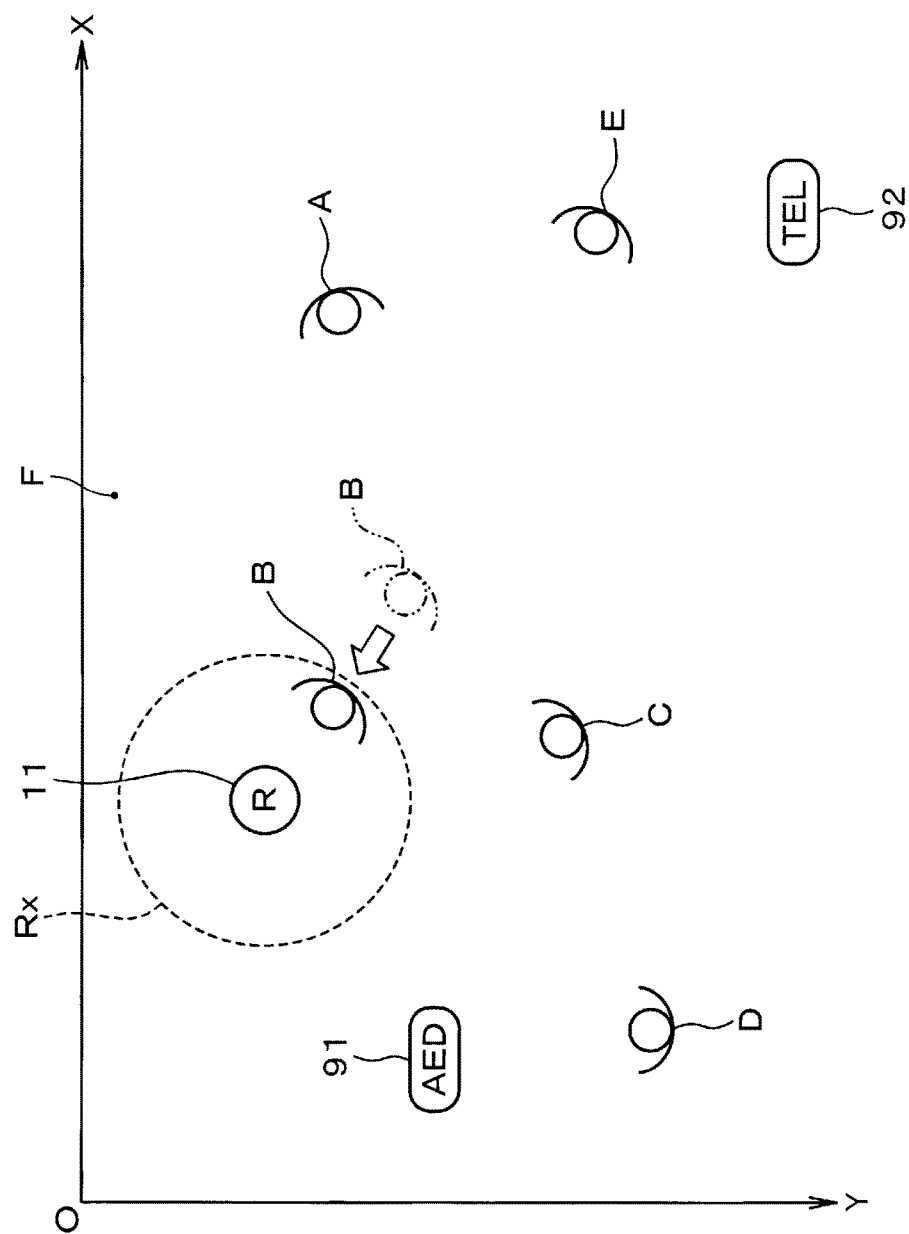

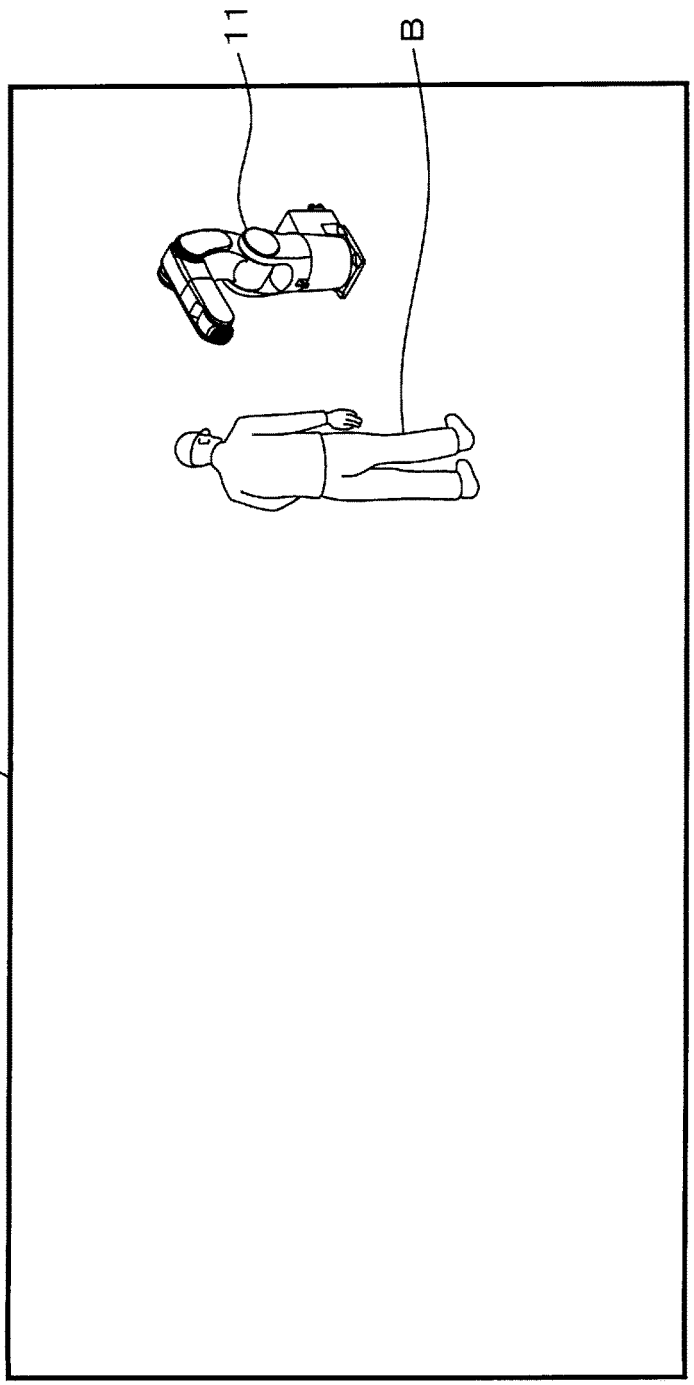

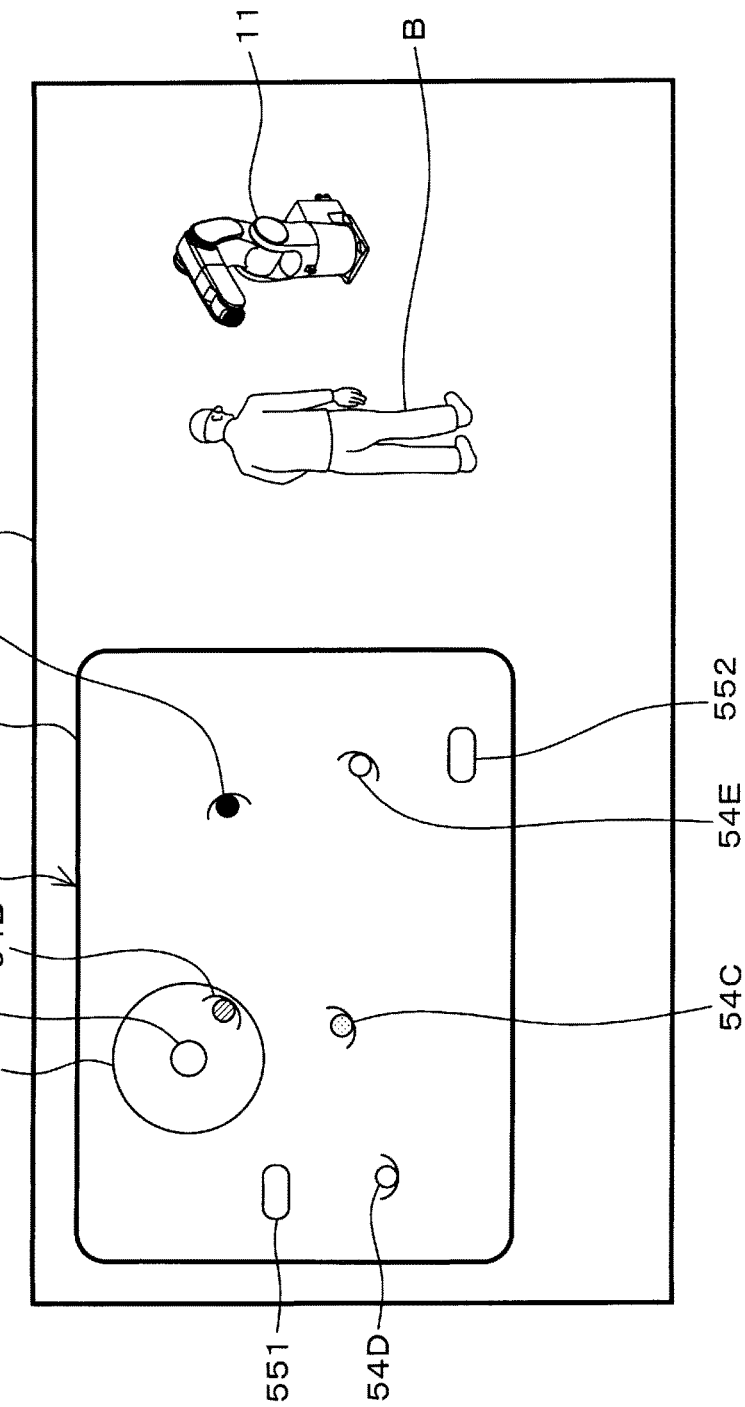

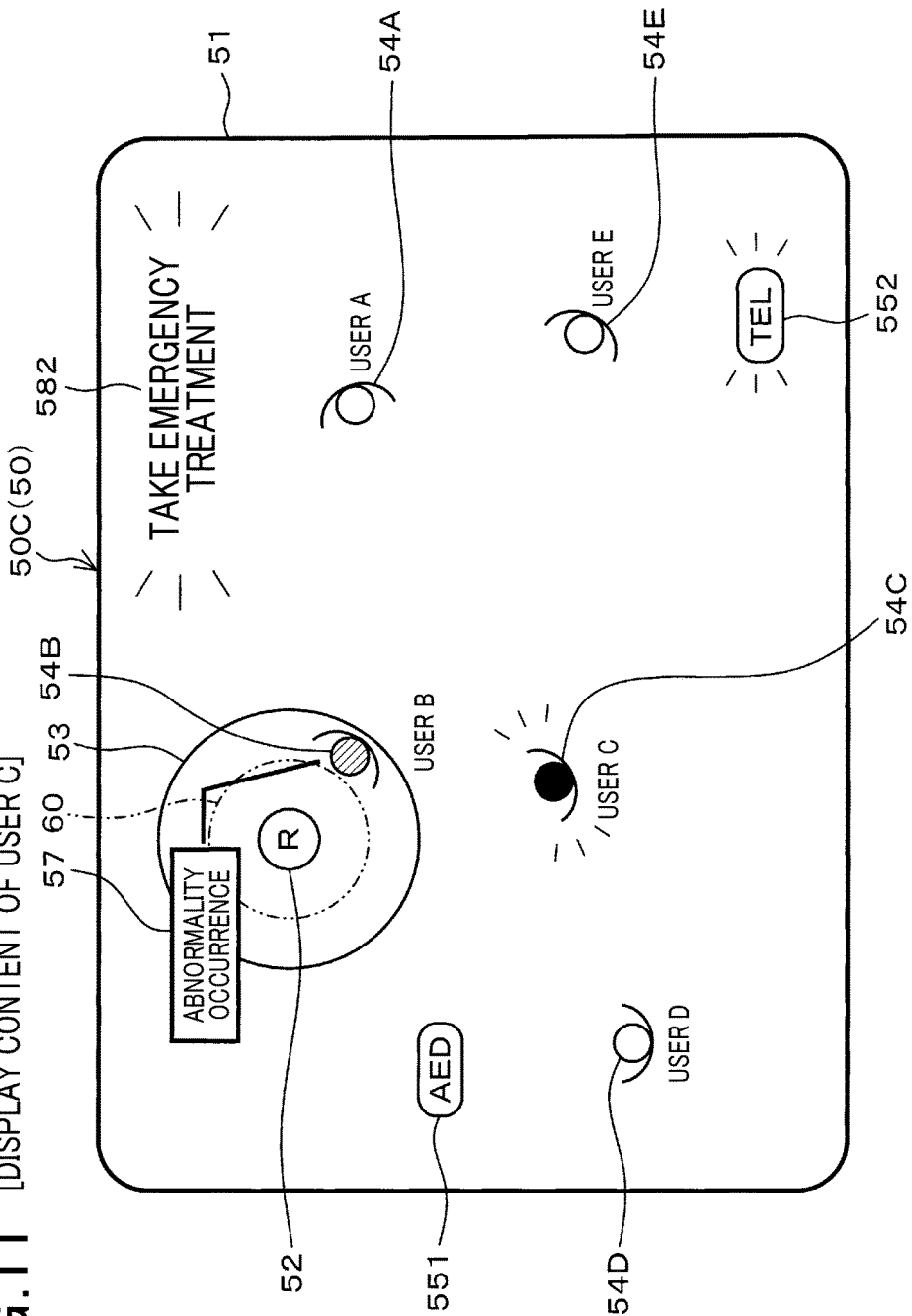

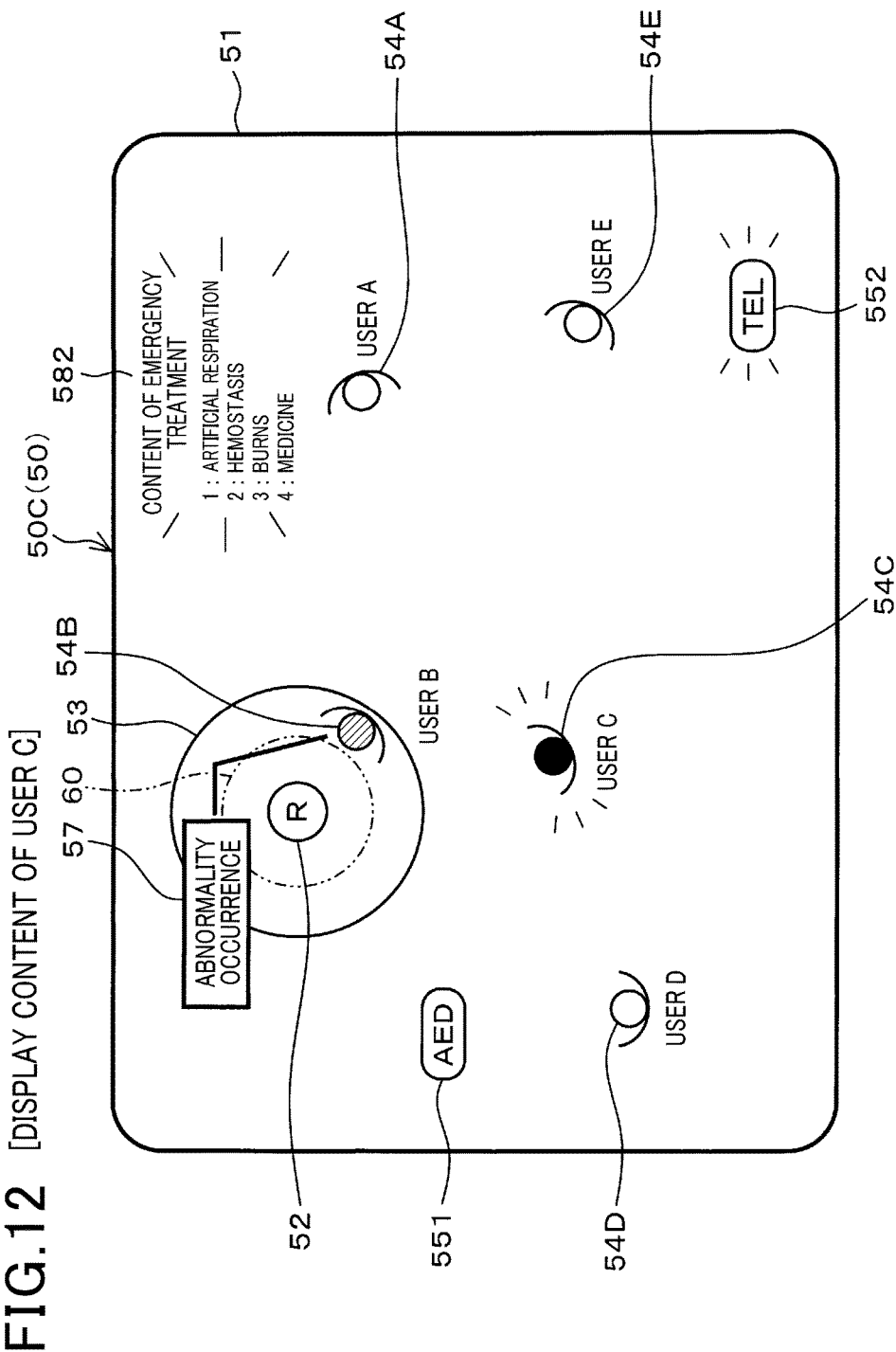

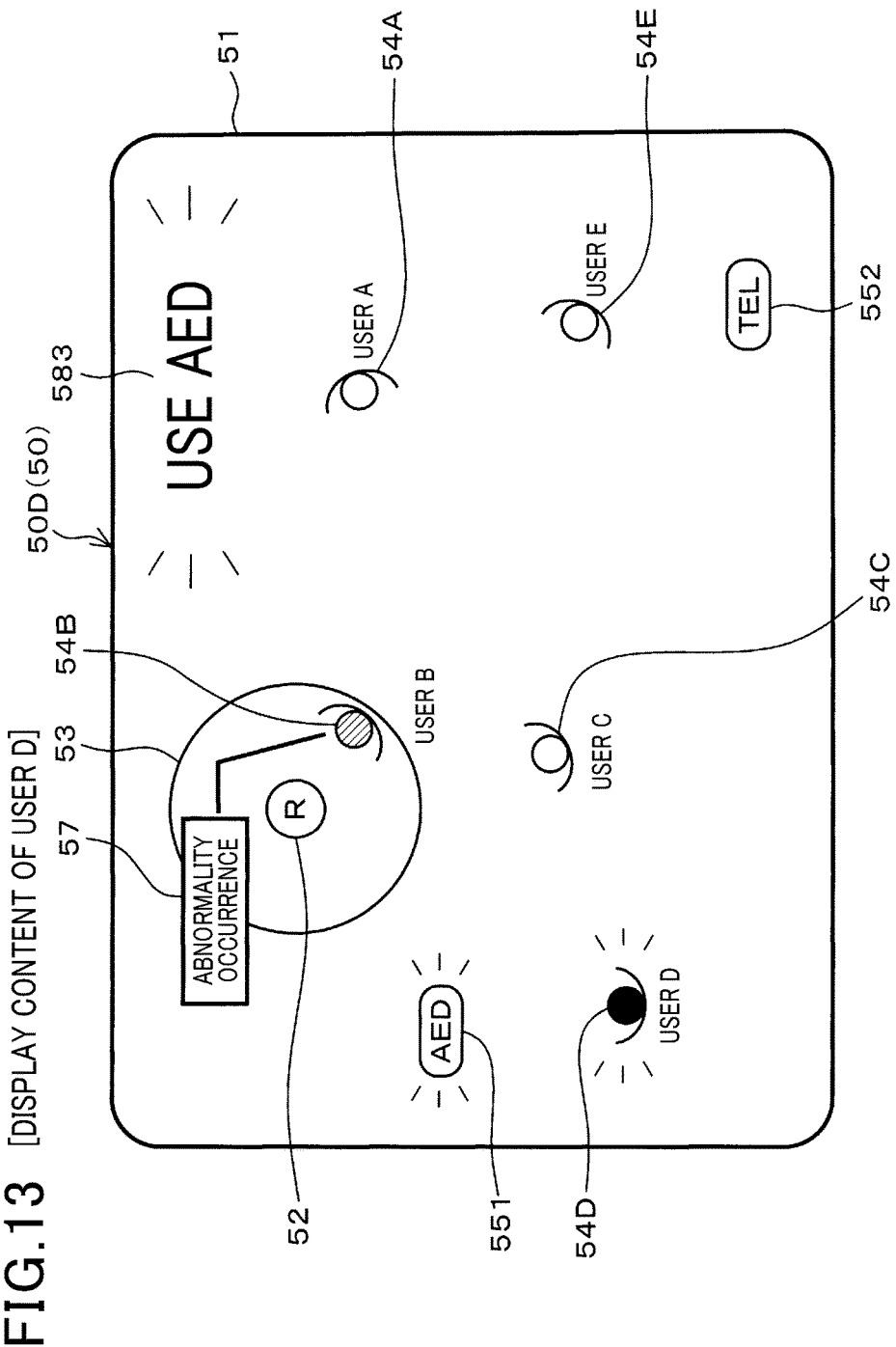
FIG.13 [DISPLAY CONTENT OF USER D]

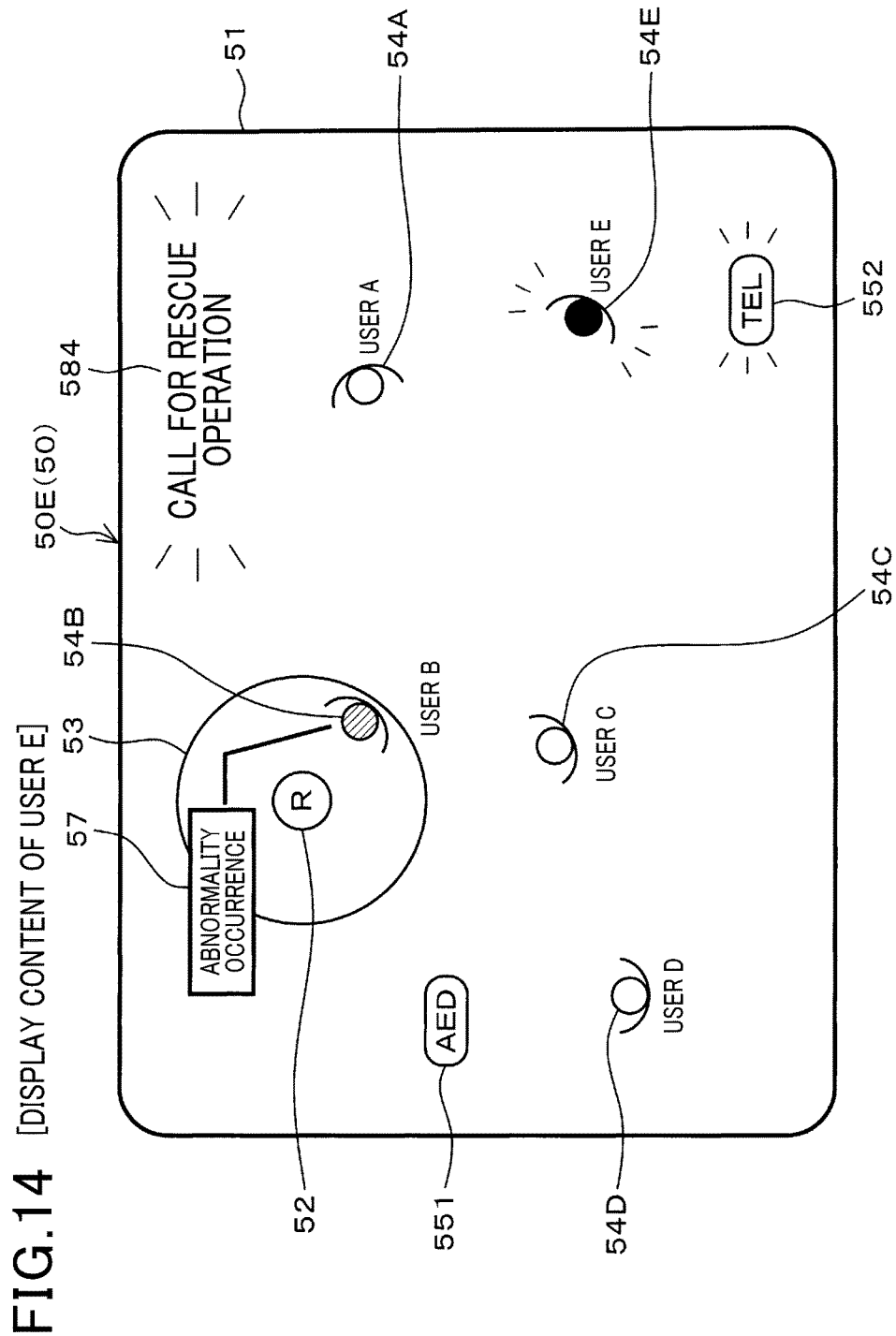
FIG.14 [DISPLAY CONTENT OF USER E]

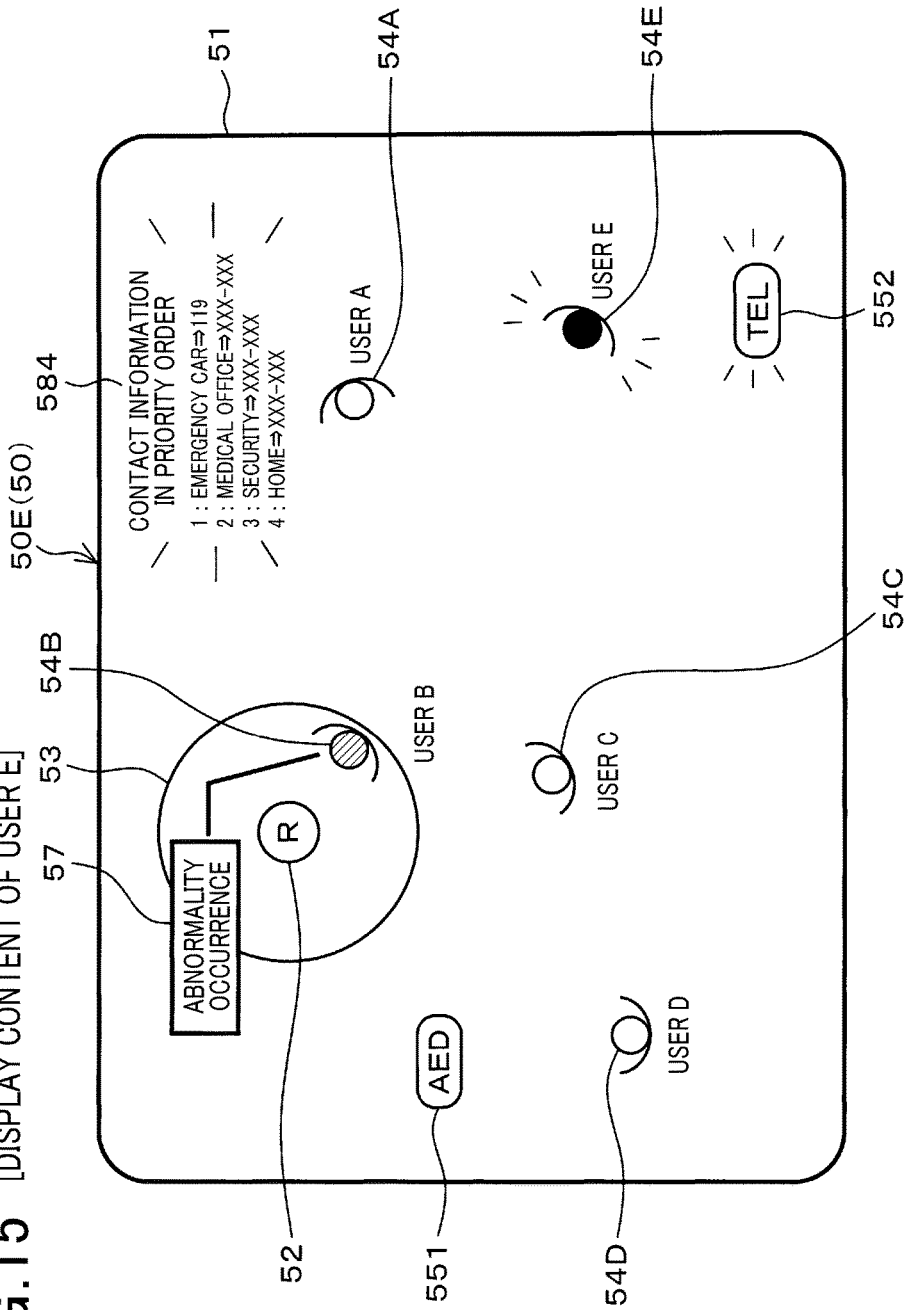
FIG.15 [DISPLAY CONTENT OF USER E]

SAFETY SYSTEM FOR INDUSTRIAL ROBOTS

CROSS-REFERENCE TO RELATED APPLICATION

This application is based on and claims the benefit of priority from earlier Japanese Patent Application No. 2015-233298 filed on Nov. 30, 2015 the description of which is incorporated herein by reference.

BACKGROUND

[Technical Field]

The present invention relates to a system to secure safety of people from a robot. More particularly, the present invention relates to a system to secure safety of people such as a worker, and the like from an industrial robot in places such as a factory and the like in which the people and the industrial robot collaborate with each other.

[Related Art]

Recently, a robotic work system in which a person and an industrial robot collaborate with each other has been continuously constructed (For example, refer to a patent literature document 1). Such the robotic work system has a tendency to exclude a conventional configuration such as a physical fence surrounding a robot. Therefore, in comparison with a work system based on the conventional configuration, it becomes much easier for the person to approach the robot in the aforementioned robotic work system, which may result in increasing the dangerousness that the robot and the person collide directly into each other.

In the case in which the physical fence surrounding the robot is not installed so as to implement collaboration work between the person and the robot, a countermeasure to prevent a collision therebetween is required. For this reason, it is important to prevent the person from approaching the robot closer than a critical distance. In this case, when the critical distance is set based on a uniform value regardless of a skill level of a worker (human being), a working environment, and a work type, following problems described hereinafter may occur.

For example, in the case of a highly-skilled worker based on his or her knowledge on a robot motion, the worker may approach the robot at a relatively close distance without causing any problem. In this case, the critical distance is set to be relatively closer, thereby having advantages of not only securing the safety of the highly-skilled worker but also securing high workability by setting an easy approach to the robot. In contrast with the aforementioned highly-skilled worker, setting the critical distance relatively close may result in a possibility of the collision between a low-skilled worker who is not aware of the robot motion and the robot, thereby increasing dangerousness therebetween. For this reason, it may be preferable to set the critical distance long to the utmost extent in consideration of the safety of the low-skilled worker. However, when the critical distance is set on the basis of a long range in accordance with the low-skilled worker, it takes more time to approach the robot such that the workability of the highly skilled worker may inversely deteriorate.

Furthermore, a risk degree of work is different depending on environments such as a time period, a working area, and the like. For example, in the case of the time period after a meal time and break, concentration of a worker becomes easier to deteriorate such that, as a result, the risk degree of the work becomes easier to be increased. In the case in which the physical fence surrounding the robot is not installed as described above, when the critical distance is set on the basis of the uniform value regardless of the skill level of the worker, the working environment, and work content, a plurality of problems may occur in terms of the safety and workability.

RELATED ART DOCUMENTS

Patent Document

[Patent Document 1] Japanese Patent Application Publication No. 2015-157352

SUMMARY

As described above, the present invention has been made in an effort to provide a system to secure safety of people such as a worker and a user in a system in which the people and a robot collaborate with each other in a state that a physical fence surrounding a working region of the robot is excluded.

An exemplary embodiment of the present invention provides a robot safety system, including: a distance acquisition unit to acquire respective distances between a robot and a plurality of people; and a critical distance setting unit to set a critical distance of the each person on the basis of at least one of personal information that the each person individually has and environment information to be set depending on a setting environment of the robot. In this case, for example, the personal information includes a plurality of pieces of information such as gender, age, working experience, a body temperature, and a pulse. The environment information, for example, includes a plurality of pieces of information such as a time period when a disaster occurred in the past and a place where the disaster occurred in the past, work content of disaster occurrence, a temperature and a room temperature at the time the disaster occurred, and the like. According to the exemplary embodiment of the present invention, the critical distance setting unit is capable of suitably adjusting and setting the critical distance depending on a skill level of a person (worker, user), a working environment, and the like. That is, the critical distance setting unit is capable of calculating the critical distance as a suitable value based on the skill level of each person and the working environment. Consequently, in comparison with a state in which the critical distance is set based on a uniform value, it is possible to accommodate both safety and workability of the people.

In addition, the robot safety system based on the aforementioned configuration may include a mounted-type monitor to be individually mounted on each person and to be capable of displaying information within a view of each person; and a control unit to control display content on the mounted-type monitor. The control unit is configured to be capable of performing a process of showing that a distance between the robot and the each person becomes less than the critical distance on the mounted-type monitor that the each person is mounting, when the distance between the robot and the each person becomes less than the critical distance.

Accordingly, information in connection with the safety of the respective people, that is to say, that any one person approaches the robot until a distance therebetween becomes less than the critical distance, may be shared among the plurality of people. Thus, when any one person approaches the robot until the distance therebetween becomes less than the critical distance, for example, another person such as a supervisor not only may warn any one person closely approaching the robot to be cautioned but also may instruct any one person to switch his or her work with one of other people such that the aforementioned countermeasures, and the like to prevent the collision therebetween may be implemented at an early stage. Consequently, according to the system in which the robot and the people collaborate with each other, it may be achieved not only to secure the safety of the respective people but also to improve the safety of all of the working regions.

According to a preferred embodiment of the present invention, the control unit may perform a process of at least displaying a first user display showing a person whose distance to the robot becomes less than the critical distance and a second user display showing a person who is closest to the person whose distance to the robot becomes less than the critical distance on the mounted-type monitor with different forms based on the respective user displays, when the distance between the robot and the person becomes less than the critical distance. In this way, the respective people may easily recognize that any one person who closely approaches the robot until the distance therebetween becomes less than the critical distance, and any one person who is closest to the person who approaches the robot until the distance becomes therebetween less than the critical distance. According to the preferred embodiment of the present invention, for example, it becomes easier for any one person such as a supervisor to instruct a person who excessively approaches the robot to switch his or her work with another person who is closest to the above-mentioned person, thereby securing the safety of the respective people in an easier way.

Here, for example, the critical distance may be set based on the gender, the age, the working experience, and the like of people such as a worker, and the like, thereby determining the critical distance which is suitably fixed for the respective people to some extent. However, the aforementioned critical distance may be adjusted before and after work or in the middle of work, depending on physical conditions of the respective people on the day he or she works.

According to another preferred embodiment of the robot safety system, the personal information is configured to include basic information that is basically not changed during a working process and biological information that describes information in associated with a living body of the person. The basic information, for example, includes the gender, the age, the working experience, and the like of the respective people. The biological information that may be changed during the working process, for example, includes a body temperature and a pulse of the person. In this way, the critical distance setting unit may set the critical distance that is suitably adjusted depending on physical conditions of the respective people on the day he or she works. Consequently, the safety of the respective people becomes much easier to be secured, thereby having an advantage of also improving the safety of all of the working regions.

Working effects other than the above-mentioned descriptions in connection with the present invention are described more in detail according to the following exemplary embodiments with reference to the accompanying drawings.

BRIEF DESCRIPTION OF THE DRAWINGS

In the drawings:

FIG. 3 is a table of an individual coefficient $\alpha i$ with respect to individual information and environment information according to an exemplary embodiment of the present invention;

FIG. 4 is a drawing schematically illustrating a concept of a critical distance according to an exemplary embodiment of the present invention;

FIG. 5 is a drawing schematically illustrating position relationships between respective people (worker, and the like) and a robot, and the like according to an exemplary embodiment of the present invention;

FIG. 6 is a drawing illustrating an example of a view point seen through a mounted-type monitor of a user A according to an exemplary embodiment of the present invention (Part 1);

FIG. 7 is a drawing illustrating an example of a view point seen through a mounted-type monitor of a user A according to an exemplary embodiment of the present invention (Part 2);

FIG. 11 is a drawing illustrating an example of an image displayed on a mounted-type monitor of a user C according to an exemplary embodiment of the present invention (Part 1);

FIG. 12 is a drawing illustrating an example of an image displayed on a mounted-type monitor of a user C according to an exemplary embodiment of the present invention (Part 2);

FIG. 13 is a drawing illustrating an example of an image displayed on a mounted-type monitor of a user D according to an exemplary embodiment of the present invention;

FIG. 14 is a drawing illustrating an example of an image displayed on a mounted-type monitor of a user E according to an exemplary embodiment of the present invention (Part 1); and FIG. 15 is a drawing illustrating an example of an image displayed on a mounted-type monitor of a user E according to an exemplary embodiment of the present invention (Part 2).

DETAILED DESCRIPTION OF THE PREFERRED EMBODIMENTS

Hereinafter, a robot safety system according to an exemplary embodiment of the present invention is described in detail with reference to the accompanying drawings.

Figure 1:
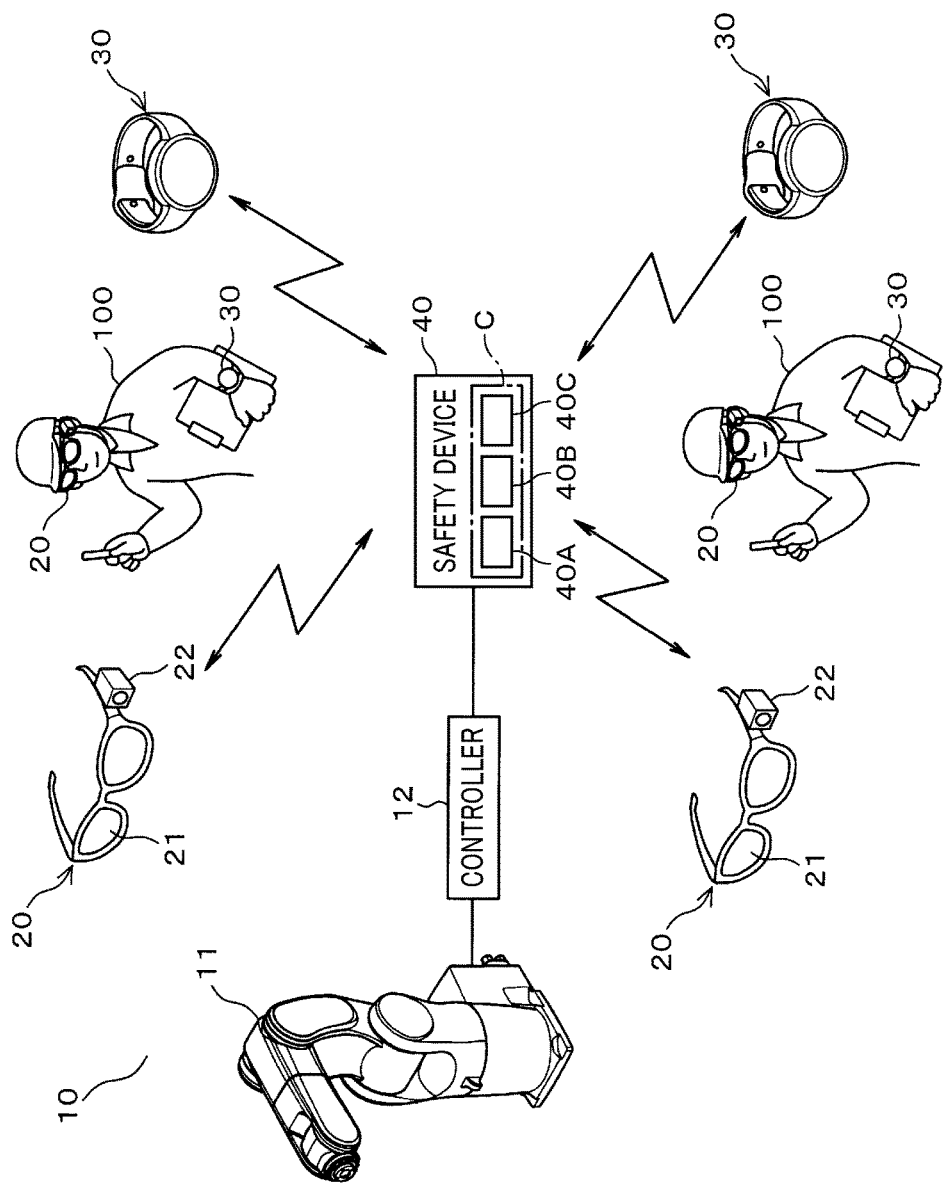
FIG. 1 is a drawing illustrating a schematic configuration of a robot safety system according to an exemplary embodiment of the present invention.
Figure 2:
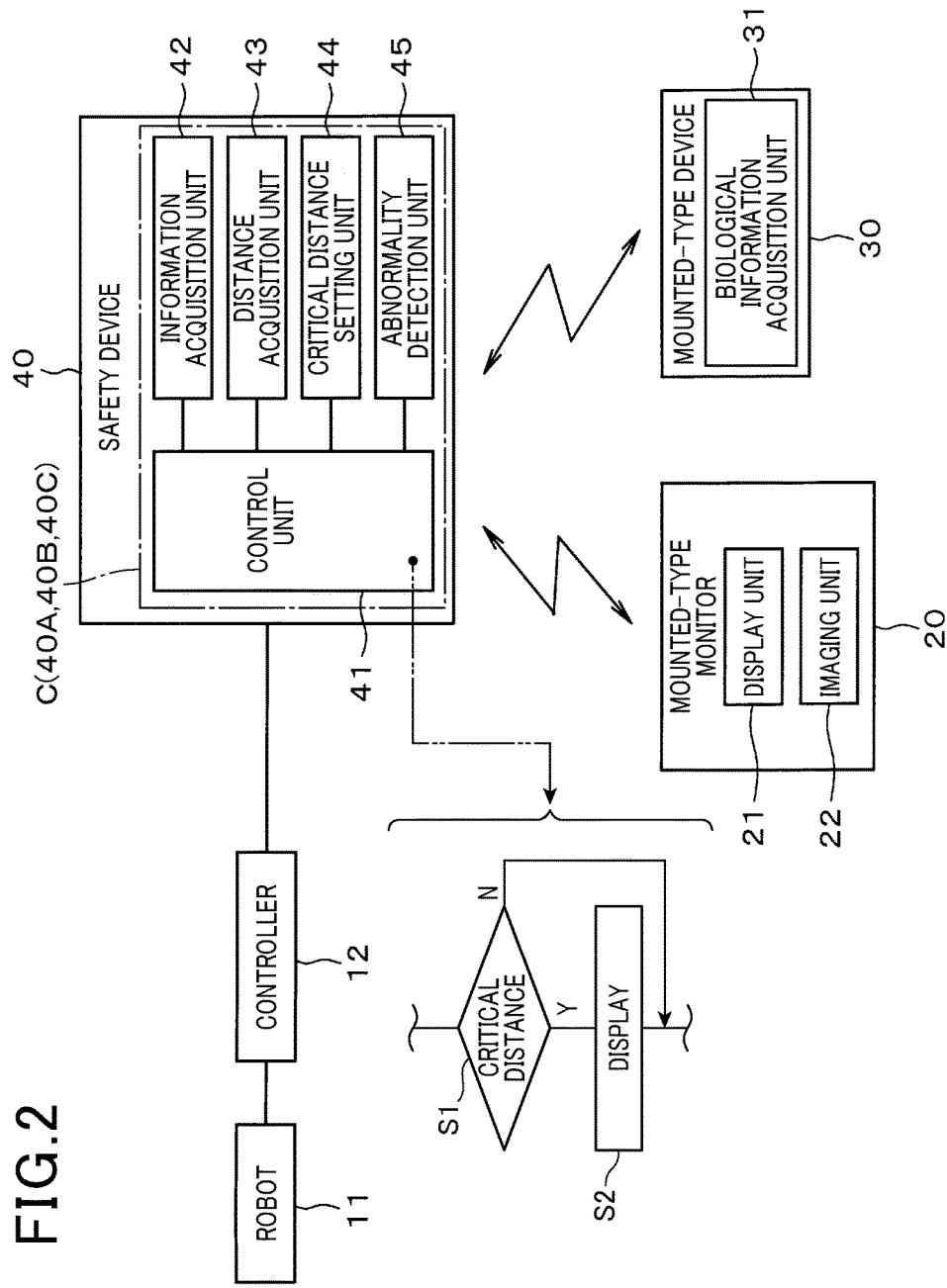
FIG. 2 is a block diagram schematically illustrating an electrical configuration of a robot safety system to an exemplary embodiment of the present invention.

As shown in FIGS. 1 and 2, an example of a system 10 (hereinafter, referred to as a robot safety system) to secure safety of people such as a worker, and the like from an industrial robot in places such as a factory and the like in which the people and the industrial robot collaborate with each other.

A robot safety system 10 is configured to include an industrial robot 11 (hereinafter, referred to as a robot), a robot controller 12, a glasses-type monitor 20, a mounted-type device 30, and a safety device 40.

Furthermore, FIG. 1 is a drawing schematically illustrating a system configuration including a robot 11 and a robot controller 12 in a first group, and a glasses-type monitor 20 and a mounted-type device 30 in a second group. However, without being limited to the aforementioned system configuration, the robot safety system 10 is capable of including the robot 11 and the robot controller 12 in a plurality of groups, and the glasses-type monitor 20 and the mounted-type device 30 in a plurality of groups. Additionally, FIG. 2 is illustrating a relationship between the robot 11 and the robot controller 12 in the first group, the glasses-type monitor 20 and the mounted-type device 30 in the second group, and a safety device 40 for better understanding and ease of description.

For example, the robot 11 is composed of a six-axis vertical multi-joint robot. A detailed description with respect to a general configuration thereof is omitted. The robot 11 has a six-axis arm which is driven by each of the servo motors. Additionally, a hand, and the like for firmly grasping, for example, a workpiece received in a pallet are provided at the tip portion of the sixth axis arm. The robot 11 is connected to the robot controller 12 via a cable (not shown) such that each axis of the sever motors is controlled by the robot controller 12.

The robot controller 12 is provided with a control circuit and a servo control unit (not shown), and a power supply, and the like. The control circuit is composed of a micro computer, which is a main part thereof. The robot controller 12 controls each of the servo motors of the robot 11 through the servo control unit according to a teaching data, various types of parameters, and the like set by a motion program memorized in advance, a teaching pendant (not shown), and the like. According to the system configuration described above, the robot controller 12 automatically performs an assembly operation, and the like in each robot 11.

The glasses-type monitor 20, which is a type of mounted-type monitor, is formed as a shape to be mounted on the head of a user (people such as a worker, and the like) like general eye glasses. As shown in FIG. 2, the glasses-type monitor 20 is provided with a display unit 21 and an imaging unit 22. The display unit 21, which is corresponding to glasses lenses, is configured as a transmission type display to be capable of displaying information such as an image, and the like. That is, the glasses-type monitor 20 is, so to speak, provided with the same configuration as smart glasses or cyber glasses.

For this reason, an image displayed on the glasses-type monitor 20 becomes overlapped with a view of the user. That is, it occurs that an actual view that the users (worker, and the like) directly see with their eyes can be seen together with a virtual image displayed on the glasses-type monitor 20. An image displayed on the display unit 21 may use image data received from the safety device 40, and also may be produced by the glasses-type monitor 20 itself based on an instruction from the safety device 40.

The imaging unit 22 is composed of a small-sized CCD camera and CMOS camera. The imaging unit 22 is built in one side part of frames of the glasses-type monitor 20 so as to have the same direction as a direction for which the face of the user is heading. The imaging unit 22 captures an image of a direction toward which the front side of the user's head is facing in a state that the user is mounted with the glasses monitor 20 on his or her head. Thus, the image captured by the imaging unit 22 has the almost same angle of a view as the view of the user. That is, the imaging unit 22 captures the almost same view the user is seeing as the view captured thereby. The glasses-type monitor 20 transmits the image data captured by the imaging unit 22 to the safety device 40.

The mounted-type device 30 is composed of a shape capable of being mounted on a body of the user. In the case of an exemplary embodiment of the present invention, the mounted-type device 30, for example, is composed as a wrist watch type capable of being mounted around the user's wrist. As shown in FIG. 2, the mounted-type device 30 is provided with a biological information acquisition unit 31. The biological information acquisition unit 31 is capable of acquiring biological information of the user mounting the mounted-type device 30, for example, a body temperature and a pulse in real time. And then, the mounted-type device 30 transmits the biological information of the user 100 acquired by the biological information acquisition unit 31 to the safety device 40 in real time.

In addition, the mounted-type device 30 is not limited to the wrist watch type. For example, the mounted-type device 30 is capable of being configured as various types such as a necklace shape to be worn around the neck, another shape to be worn around the leg, and the like. Furthermore, the mounted-type device 30 may be configured to be built in the glasses-type monitor 20. In this case, the mounted-type device 30 is capable of being configured as a camera for monitoring eyeball movement and a pupil size of the user 100 and an electrode for measuring brain waves of the user 100, and the like.

The robot controller 12, the glasses-type monitor 20, and the mounted-type device 30 are respectively connected to the safety device 40 wirelessly or by wire. The safety device 40 is configured to be capable of acquiring a variety of specifiable information such as a motion state of the robot 11 from the robot controller 12 and a control state depending on the robot controller 12. Accordingly, the safety device 40 is capable of acquiring a rotation angle of the arm of the robot 11, an electric conduction state of the motor, motion information showing the motion state of the robot 11, and control information showing the control state of the controller 12 in real time.

Furthermore, the safety device 40 is capable of producing 3D model image data provided by performing a modeling process on a current shape of the robot 11, that is to say, a posture thereof in a three-dimensional way on the basis of the information of each robot 11 acquired from the robot controller 12. Additionally, as shown in FIG. 5, the safety device 40 memorizes a region in which the robot 11 is installed, for example, a coordinate of the robot 11, that is say, an installation position thereof, with respect to a two dimensional coordinate system of which origin position is a reference position 0 in a factory. In addition, the safety device 40 also memorizes coordinates of the facilities installed around the robot 11 such as a life-saving apparatus 91 of automated external defibrillator (AED) and the like, a telephone 92 and the like, that is to say, the safety device 40 memorizes the installation position of the robot 11.

Additionally, as shown in FIG. 2, the safety 40 is configured to be provided with a computer C including CPU (Central Processing Unit) 40 in charge of processing arithmetic operation, ROM (Read-Only Memory) 40B, and RAM (Random Access Memory) 30C, and is also configured to be capable of communicating with an external device. According to the above-mentioned operation, the CPU40A reads a control program that is stored into ROM40B in advance and a processing program to secure safety from a robot in the corresponding working region and further implements the programs described above in order. For this reason, the ROM40B performs a function as a non-transient computer readable recording medium. The RAM40C is performed to store temporary data during the processing stage in which the CPU40A implements the program.

According to the process of the computer C, the safety device 40 is functionally provided with a control unit 41, an information acquisition unit 42, a distance acquisition unit 43, a critical distance setting unit 44, and an abnormality detection unit 45.

Furthermore, the information acquisition unit 42, the distance acquisition unit 43, the critical distance setting unit 44, and the abnormality detection unit 45 may be implemented as hardware, for example, in a form of an integrated circuit with the control unit 41.

The information acquisition unit 42, that is to say, the computer C, is configured to be capable of performing a process of acquiring personal information and environment information from outside. According to the exemplary embodiment of the present invention, the personal information means user's specific information that each user (worker) 100 has individually, and is configured to include basic information and the biological information. The basic information means information that is not changed during the working day as a principle among the user's specific information, for example, a plurality of pieces of information such as gender, age, working experience, and the like of the user are included therein. The basic information is an indicator showing a skill level and a high or low level of a technique of the user with respect to the corresponding work. The biological information means information that may be changed during the working day among the user's specific information. For example, a body temperature, a pulse, and the like of the user 100 are included therein. The biological information is an indicator describing that a physical condition of the user 100 is good or bad at the current moment or during the corresponding working day. The environment information includes a plurality of pieces of information, for example, such as a time period when a disaster occurred in the past and a place where the disaster occurred in the past, work content of disaster occurrence, and a temperature and a room temperature at the time the disaster occurred. The environment information is an indicator showing whether a current environment in which the user 100 in positioned may cause disaster easily or not.

Furthermore, the information acquisition unit 42 is configured to be capable of acquiring the following pieces of basic information. When the glasses-type monitor 20 and the mounted-type device 30 are individual's private ones, that is to say, when the glasses-type monitor 20, the mounted-type device 30, and each user 100 are connected therebetween in advance, basic information of an owner becomes memorized in the glasses-type monitor 20 and the mounted-type device 30, and then the information acquisition unit 42 reads the basic information. According to the system configuration described above, the information acquisition unit 42 is capable of acquiring the basic information of each user 100 in a state that the glasses-type monitor 20, which is the mounted-type device 30, and each user 100 are connected therebetween.

In the case in which the glasses-type monitor 20 and the mounted-type 30 are shared with a plurality of people, when the user 100 starts to use the glasses-type monitor 20 and the mounted-type 30, it is performed to process connecting the glasses-type monitor 20 and the mounted-type 30 with the basic information of the user 100. In this case, for example, an input unit (not shown) is built in the safety device 40. Furthermore, the user 100 inputs his or her basic information therein by using the input unit, and also registers an identification number of the glasses-type monitor 20 and the mounted-type 30. In this way, the information acquisition unit 42 is capable of acquiring the basic information of each user 100 in a state that the glasses-type monitor 20, the mounted-type 30, and the user 100 are connected therebetween.

In addition, the input unit (not shown) may be, for example, a key board and a touch panel on which the user 100 can directly input his or her basic information, and for example, a card reader capable of reading the basic information input and memorized in an employee identification card, and the like. Furthermore, the information acquisition unit 42 may acquire the basic information of each user 100 and each name of each user 100.

Furthermore, the information acquisition unit 42 is configured to be capable of acquiring the biological information of the user 100 by receiving the biological information acquired from the biological information acquisition unit 31 of the mounted-type device 30. For example, the information acquisition unit 42 is capable of acquiring the environment information based on the following method. That is, the user 100 suitably renews the environment information in the safety device 40 and memorizes the corresponding environment information therein. And then, the information acquisition unit 42 acquires the environment information by reading out the environment information being memorized in the safety device 40. Additionally, the safety device 40 is connected to a network (not shown), and a data server (not shown) memorizing the environment information is disposed on the network. In the case of the information acquisition 42, the environment information may be acquired through the network from the data server.

The distance acquisition unit 43, that is to say, the computer C, is configured to be capable of performing a process of acquiring a distance between the robot 11 and each user 100, and a distance between each of the facilities 91 and 92 and each user 100. Furthermore, according to the exemplary embodiment of the present invention the distance acquisition unit 43 is configured to be capable of performing a process of acquiring the distance between the robot 11 and each user 100, and the distance between each of the facilities 91 and 92, and each user 100, for example, on the basis of position information of each user 100. That is, for example, as shown in FIG. 5, the distance acquisition 43 acquires a coordinate of the robot 11 based on a two-dimensional coordinate system of a region in which the robot 11 and each of the facilities 91 and 92 are installed. And then, the distance acquisition unit 43 calculates the distance between the robot 11 and each user 100 and the distance between each of the facilities 91 and 92 and each user 100 from a coordinate of each user 100 and the robot 11, and a coordinate of each user 100 and the respective facilities 91 and 92.

The coordinate of each user 100, that is to say, position information of the user 100, is able to be acquired by installing, for example, a small-sized GPS (Global Positioning System) on the glasses-type monitor 20. In addition, the position information of the user 100 may not directly specify a position like a GPS unit. For example, the position information of the user 100 may be configured to acquire a movement trajectory of the user 100 from a reference position 0 of an entrance of a factory, and the like, and also may be configured to indirectly specify a position based on a displacement amount with respect to the reference position 0.

The critical distance setting unit 44, that is to say, the computer C, is capable of performing a process of setting a critical distance Lx on the basis of at least one of the personal information of the user 100 and the environment information acquired from the distance acquisition unit 43. In the case of the exemplary embodiment of the present invention, the critical distance setting unit 44 sets the critical distance Lx of each user 100 on the basis of both the personal information and the environment information. As shown in FIG. 4, the critical distance Lx is a distance on the basis of the robot 11 on a floor surface F. As described in formula (1) below, the critical distance Lx is a value calculated by multiplying a reference distance L by a value adding "1" to an integration value $\Sigma\alpha i$ of an individual coefficient $\alpha i$. That is, the critical distance Lx is a total value calculated by adding the reference distance L to a value that is calculated by multiplying the reference distance L by the integration value $\Sigma\alpha i$ of the individual coefficient $\alpha i$.

$$Lx=Lx(1+\Sigma\alpha i) \quad (1)$$

In this case, the reference distance L is a distance calculated by adding a predetermined distance D2 to a movable distance D1 of the robot 11. So, the distance becomes an initial value of the critical distance Lx, that is to say, the integration value $\Sigma\alpha i=1$. Furthermore, a distance more than the critical distance is referred to as a safety distance. The movable distance D1 is a distance from the robot 11 to a tip portion of an arm in a state that all of the arms of the robot 11 are horizontally stretched out. The predetermined distance D2 is determined depending on motion speed, and the like of the robot 11. For example, even when a general user approaches the robot 11 instantly, a distance therebetween does not reach the movable distance D1 of the robot 11. In other words, the critical distance Lx is a distance calculated by adding a safety margin to be set respectively to every individual person and in every environment in which the robot 11 is installed to the movable distance D1 of the robot 11. In this case, an inner region of the critical distance based on the robot 11 is referred to as a critical region. Furthermore, an outer region of the critical distance based on the robot 11 is referred to as a safety region.

The critical distance setting unit 44, that is to say, the computer C, sets the individual coefficient $\alpha i$ on the basis of the personal information of each user 100 and the environment, and is configured to be capable of setting the individual coefficient $\alpha i$ as a value that is adjusted to the user 100 practically performing a work and the environment in which the robot 11 is installed. For example, as shown in FIG. 3, the individual coefficient $\alpha i$ is plurally set for the personal information and the environment information. As the integration value $\Sigma\alpha i$ of the individual coefficient $\alpha i$ is greater, the critical distance Lx also becomes long. In addition, as shown in FIG. 3, individual coefficients $\alpha 1$ to $\alpha 3$ are individual coefficients based on the basic information of the personal information, and individual coefficients $\alpha 4$ and $\alpha 5$ are individual coefficients based on the biological information of the personal information. Also, individual coefficients $\alpha 6$ and $\alpha 7$ are individual coefficients based on the environment information. For example, under the state that in the case of the user 100, the gender is a male, the age is in his fifties, the working experience is more than 20 years, the body temperature is a normal temperature, and the pulse is under normal conditions, meanwhile, in the case of the user 100, the gender is a female, the age is in her twenties, the working experience is less than 5 years, the body temperature is more than "the normal temperature +0.5° C.", and the pulse is on the increase when staring work, and also a coefficient based on the environment information is not set, thereby becoming $\alpha 6=\alpha 7=0$, the integration value $\Sigma\alpha i$ of the individual coefficient $\alpha i$ becomes 1.1. In this case, the critical distance Lx=the reference distance L×2.1. That is, the critical distance Lx set to the user 100 becomes 2.1 times distance of the reference distance L.

The abnormality detection unit 45, that is to say, the computer C is configured to be capable of performing a process of detecting the abnormalities happening to the user 100 such as a fall of the user 100, a collision between the user 100 and the robot 11, and the like detected through the glasses-type 20 monitor or the mounted-type device 30 the user 100 is mounting. For example, when the biological information of the user 100 to be acquired from the biological information acquisition unit 31 of the mounted-type device 30 becomes an abnormal value, the abnormality detection unit 45 is capable of detecting the abnormality happening to the user 100. Furthermore, for example, as described hereinafter, the abnormality detection unit 45 is capable of detecting the abnormality happening to the user 100. That is, a sensor capable of detecting an impact provided to the user 100 such as, for example, an acceleration sensor and a gyro sensor may be installed. And then, when an excessive impact, that is to say, an impact that is different from a normal time is provided to the glasses-type monitor 20 or the mounted-type device 30 and the excessive impact is detected, the abnormality detection unit 45 determines that the abnormality has happened to the user 100.

Next, operation of the aforementioned configuration is described with reference to the accompanying drawing from FIGS. 5 to 15. In addition, in the following descriptions, it is assumed and described that five users including the users A to E are present within a working region on the floor surface F of a factory, and the like (the working region is described by using rectangular Cartesian coordinates X Y on the floor surface). Furthermore, the user A is set as a supervisor of the working region. Information with respect to the supervisor of the working region is registered in the safety device 40. Additionally, characters including A to E in connection with the users A to E not only mean each name of the users A to E but also are used as signs indicating each of the users A to E in drawings. In this case, the critical distance Lx that is individually different depending on each of the users A to E is set. That is, in FIG. 3, the individual coefficients $\alpha 1$ to $\alpha 5$ based on the personal information are set with each of the values that is different depending on each of the users A to E. Furthermore, since the working environments of each of the users A to E are almost same, the individual coefficients $\alpha 6$ and $\alpha 7$ based on the environment information are set with the same values as the ones of each of the users A to E.

The control unit 41, that is to say, the computer C, determines whether each distance between the robot 11 and the users A to E becomes less than each critical distance Lx of the users A to E or not at step S1 in FIG. 2. Furthermore, when the critical distance Lx is determined at step S1 (YES) in accordance with the determination of the step S1, the control unit 41 is capable of showing that each distance between the robot 11 and the users A to E becomes less than the critical distance Lx on the display unit 21 of the glasses-type monitor 20 that each of the users A to E is mounting at step S2 in FIG. 2. The steps S1 and S2 repeat a predetermined processing routine and are repeatedly performed at each given time.

That is, when one of the users A to E has entered the critical region of the robot 11, the control unit 41 is capable of showing that one of the users A to E has entered the critical region of the robot 11 on the glasses-type monitor 20.

For example, a circle with broken lines centered at the robot 11 in FIG. 5 shows the critical distance Lx set to the user B. That is, the circle with broken lines centered at the robot 11 shown in FIG. 5 shows a critical region Rx set to the user B. With respect to the user B shown in alternate long and two short dashes line in FIG. 5, when a distance between the user B and the robot 11 is the safety distance, that is to say, when the user B does not enter the critical distance Rx of the robot 11, as shown in FIG. 6, nothing is displayed on the glasses-type monitor 20 of each of the users A to E. Meanwhile, when the critical distance Lx between the user B and the robot 11 becomes less than the critical distance Lx, that is to say, when the user B has entered the critical region Rx of the robot 11, the control unit 41 as shown in FIG. 7, displays an image 50 on the glasses-type monitor 20 of each of the users A to E. In this case, the image 50, for example, is displayed on a corner of the display unit 21. Furthermore, FIG. 7 is a drawing illustrating that display content is displayed on the glasses-type monitor 20 of the user A.

Figure 8:
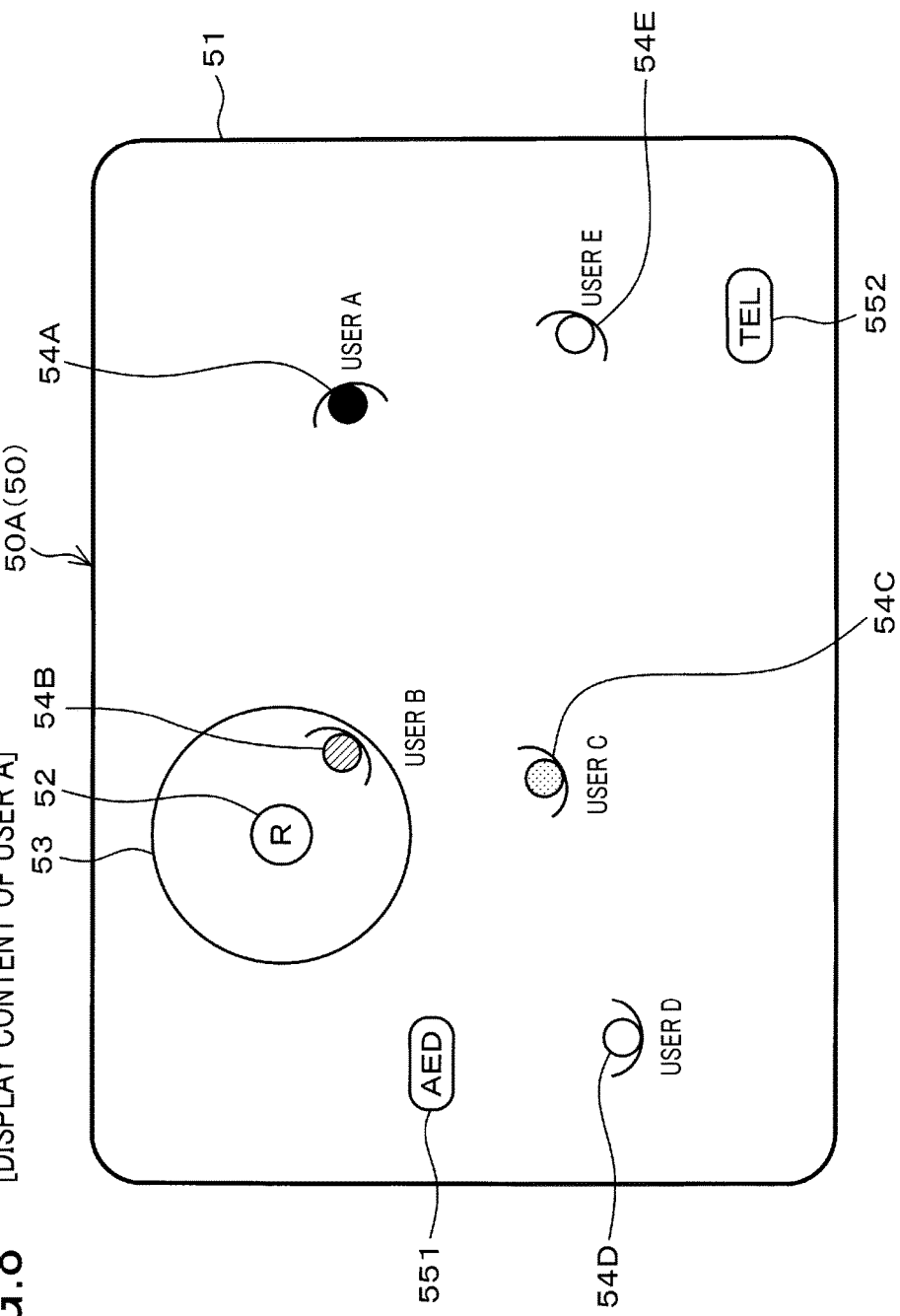
FIG. 8 is a drawing illustrating an example of an image displayed on a mounted-type monitor of a user A according to an exemplary embodiment of the present invention.

For example, as shown in FIG. 8, the image 50 is configured with an outer frame 51 showing the working region, a robot display 52 showing the robot 11, a region display 53 showing the critical region Rx of the robot 11, user displays 54A to 54E showing the users A to E, facility displays 551 and 552 showing facilities, and the like. In addition, the facility display 551 shows the life-saving apparatus 91, the facility display 552 shows the telephone 92. Furthermore, when the user displays 54A to 54E described as a general term, simply they become the user display 54. Additionally, the user displays 54A to 54E may include character strings describing each name of the user A, the user B, and the like.

The control unit 41 displays the user display 54 that shows a user mounting the glasses-type monitor 20 on which the image 50 is displayed, the user display 54 that shows a user positioned less than the critical distance Lx, the user display 54 that shows a user who is closest to the user positioned less than the critical distance Lx, and the user display 54 that shows a user excluding the aforementioned users with respectively different display forms. For example, the control unit 41 shows the user display 54 showing a user of the glasses-type monitor 20 on which the image 50 is displayed with a green color, and the user display 54 showing a user positioned less than the critical distance Lx with a red color. In addition, the control unit 41 shows the user display 54 showing a user who is closest to the user positioned less than the critical distance Lx with a blue color, and shows the user display 54 showing a user excluding the aforementioned users with a white color. Furthermore, when the user mounted with the glasses-type monitor 20 on which the image 50 is displayed is positioned less than the critical distance Lx from the robot 11, the user display 54 showing the corresponding user shows that the corresponding user is positioned less than the critical distance Lx with a red color as a top priority.

Figure 9:
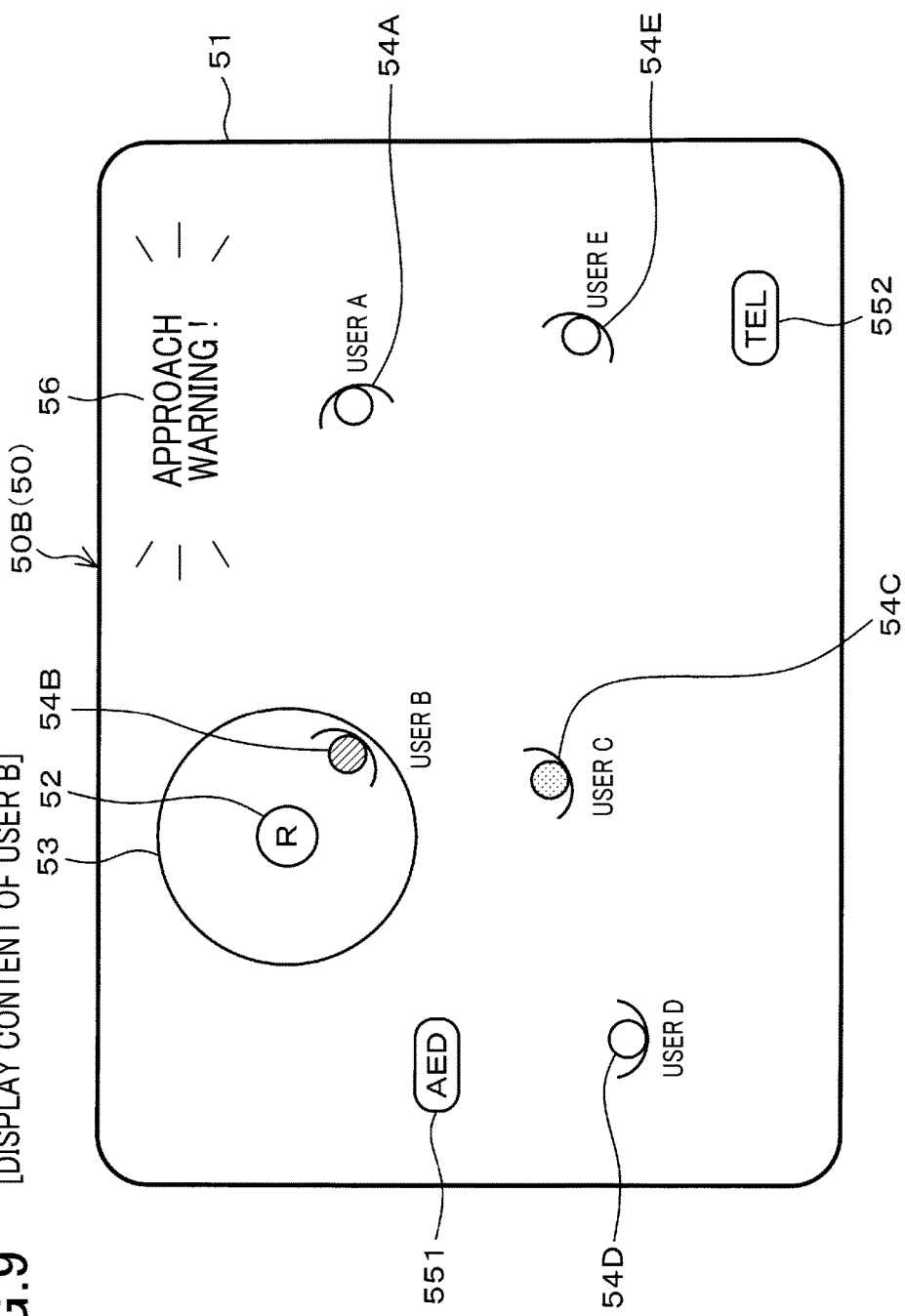
FIG. 9 is a drawing illustrating an example of an image displayed on a mounted-type monitor of a user B according to an exemplary embodiment of the present invention.
Figure 10:
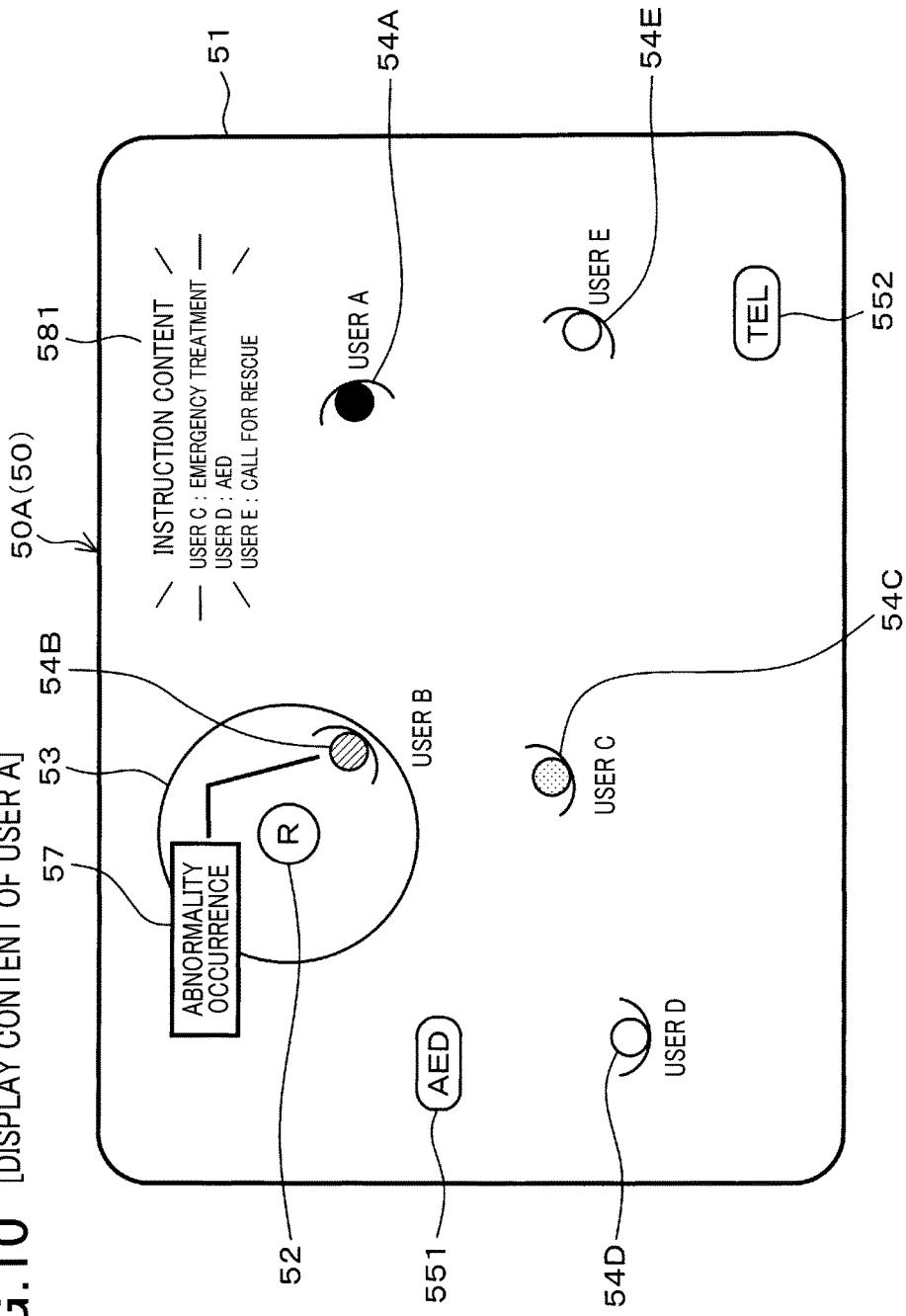
FIG. 10 is a drawing illustrating an example of an image displayed on a mounted-type monitor of a user A according to an exemplary embodiment of the present invention, when abnormality has happened.

That is say, specific contents of the image 500 displayed on the display unit 21 are different depending on each of the users A to E. Furthermore, an image 50A shown FIGS. 8 and 10 is the image 50 displayed on the glasses-type monitor 20 of the user A. An image 50B shown FIG. 9 is the image 50 displayed on the glasses-type monitor 20 of the user B. An image 50C shown in FIGS. 11 and 12 is the image 50 displayed on the glasses-type monitor 20 of the user C. An image 50D shown FIG. 13 is the image 50 displayed on the glasses-type monitor 20 of the user D. And, an image 50E shown in FIGS. 14 and 15 is the image 50 displayed on the glasses-type monitor 20 of the user E.

In this case, as shown in FIG. 8, with respect to the image 50A displayed on the glasses-type monitor 20 of the user A, the control unit 41 shows the user display 54 showing the user A mounted with the glasses-type monitor 20 on which the image 50 is displayed with a green color, and shows the user display 54B showing the user B positioned less than the critical distance Lx with a red color. Furthermore, the control unit 41 shows the user display 54 C showing the user C who is closest to the user B with a blue color, and shows user displays 54D and 54E showing the users D and E excluding the users A to C with a white color. According to the image 50, for example, the user A, the supervisor, is able to instruct the user C, who is closest to the user B, shown with the blue color to switch his or her work with the user B shown with the red color.

In addition, the control unit 41, as shown in the image 50 of FIG. 9, displays an notice displaying 56 such as a "approach warning", and the like on the glasses-type monitor 20 that the user B, who is positioned less than the critical distance Lx, is mounting. The user B is able to promptly recognize that the user B himself or herself closely approaches the robot 11 such that the user B is positioned less than the critical distance Lx by watching the attention display 56 of the image 50B. Accordingly, when the distance between the user B and the robot 11 becomes greater than the critical distance, that is to say, the user B is positioned out of the critical region Rx of the robot 11, the control unit 41 does not display the image 50 that was being displayed on the glasses-type monitor 20 of each of the users A to E.

Furthermore, when the control unit 41 detects that the abnormality has happened to a certain user from the abnormality detection unit 45, the control unit 41 is capable of performing a process of displaying information to report that the abnormality has happened to the certain user on the glasses-type monitor 20 that the users excluding the certain user to whom the abnormality has happened are mounting. In this case, the control unit 41 displays the user display 54 showing the certain user to whom the abnormality has happened on the mounted-type monitor 20 that other users excluding the certain user to whom the abnormality has happened are mounting with a display form that is different from when the abnormality does not happen. Additionally, the control unit 41 displays instruction content that instructs each of the users excluding the certain user to whom the abnormality has happened to take action on the glasses-type monitor 20 that each of the users is mounting. The control unit 41 individually changes the instruction content displayed on the glasses-type monitor 20 of each of the users depending on each user position.

The following example is described when the abnormality such as the fall happens to the user B. when the user B falls down, the abnormality detection unit 45 detects an impact provided to the user B and also detects that the abnormality has happened to the user B. That is, the control unit 41 displays the abnormality happening to the user B and individual instruction content with respect to each of the users A, and C to E on the glasses-type monitor 20 of each of the users A, and C to E. In this case, when the user B has a usual day, that is to say, the abnormality does not happen, the control unit 41 displays the user display 54B of the user B, for example, with the green color. Meanwhile, when the abnormality has happened to the user B, the control unit 41 displays the user display 54B of the user B, for example, with the red color of which color is different from the color of the normal time.

Furthermore, in this case, as shown in FIG. 5, the user C is closest to the user B among each of the users A, and C to E excluding the user B. Additionally, the user D is closest to the life-saving apparatus 91 among each of the users A, and C to E excluding the user B. Also, the user E is closest to the telephone 92 among each of the users A, and C to E excluding the user B. Accordingly, the control unit 41 instructs the user C to perform emergency treatment for the user B, instructs the user D to go for taking the life-saving apparatus 91 disposed at a near or close distance, and instructs the user E to make a phone call for emergency services by using the telephone disposed at a near or close distance.

Specifically, as shown in FIG. 10, the control unit 41 displays an information display 57 of "accident occurrence" showing that the abnormality has happened to the user B and an instruction information 581 showing the instruction content with respect to each of the users C to E on the glasses-type monitor 20 of the user A, the supervisor. In this case, the control unit 41 noticeably displays the instruction information 581 by making the instruction information 581 alternately flash on and off. In this way, the user A, the supervisor, is able to easily recognize what type of the instruction is being provided to each of the users C to E.

As shown in FIG. 11, the control unit 41 displays the information display 57 of "accident occurrence" showing that the abnormality has happened to the user B, and the instruction information 582 of "take emergency treatment" showing the instruction content with respect to the user C on the glasses-type monitor 20 of the user C. In this case, the control unit 41 noticeably displays the instruction information 582 and the user display 54 C by making the instruction information 582 and the user display 54 C alternately flash on and off. In this way, the user C, the supervisor, is able to promptly know his or her next action to be taken, that is to say, that the user C himself or herself takes the emergency treatment for the user B.

Furthermore, as shown in FIG. 12, after displaying the instruction information 582 for a fixed period, for example, for several seconds, the control unit 41 displays item information 591 showing items such as "artificial respiration", "hemostasis", "burns", "medicine", and the like in accordance with types of corresponding accidents on the glasses-type monitor 20 of the user C. The user selects a suitable item from the item information 591 in accordance with the abnormality of the user B by using an operation switch (not shown), and the like. That is, even though a detailed drawing is not illustrated, the control unit 41 displays a drawing, and the like showing the suitable treatment method in accordance with the selected item on the glasses-type monitor 20 of the user C. In this way, the user C is able to make sure of the treatment method from the drawing, and the like. In addition, the item information 591, which is not limited to the user C, may be displayed on the glasses-type monitor 20 of the user A, the supervisor such that the user A may also select a suitable item.

In addition, FIG. 11 is a drawing illustrating that the region display 53 shows the critical distance Lx set to the user B, and the region display 60 shows the critical distance Lx set to the user C. That is, in this case, the control unit 41, as shown in FIG. 11, displays not only the region display 53 showing the critical distance Lx set to the user B to whom the abnormality has happened but also the region display 60 showing the critical distance Lx set to another user to whom the abnormality does not happen excluding the user B, for example the user C heading for the rescue on the mounted-type monitor 20 that the user C is mounting.

The control unit 41, as shown in FIG. 12, displays the information display 57 of "accident occurrence" showing that the abnormality has happened to the user B, and the instruction information 583 of "use AED" showing the instruction content with respect to the user D on the glasses-type monitor 20 of the user D. In this case, the control unit 41 noticeably displays the instruction information 583 by making the instruction information 583 alternately flash on and off. In this way, the user D is able to promptly know his or her next action to be taken, that is to say, the user D himself or herself goes to take the life-saving apparatus 91 and use the life-saving apparatus 91 for the user B. Furthermore, the control unit 41 more noticeably displays the user display 54D and the facility display 551 by making the user display 54D and the facility display 551 alternately flash on and off. In this way, the user D is able to make sure of a position relationship between the user D himself or herself and the life-saving apparatus 91 in an easy way, thereby having an advantage of promptly going for the life-saving apparatus 91.

The control unit 41, as shown in FIG. 13, displays the information display 57 of "accident occurrence" showing that the abnormality has happened to the user B, and the instruction information 584 of "call emergency services" showing the instruction content with respect to the user E on the glasses-type monitor 20 of the user E. In this case, the control unit 41 noticeably displays the instruction information 584 by making the instruction information 584 alternately flash on and off. In this way, the user D is able to easily know his or her next action to be taken, that is to say, that the user D himself or herself makes a phone call for the emergency services by using the telephone 92. Furthermore, the control unit 41 more noticeably displays the user display 54E and the facility display 552 by making the user display 54E and the facility display 552 alternately flash on and off. In this way, the user E is able to make sure of a position relationship between the user D himself or herself and the telephone 92 in an easy way, thereby promptly arriving at a place in which the telephone 92 is disposed.

Furthermore, after displaying the instruction information 584 for a fixed period, for example, for several seconds, as shown in FIG. 15 the control unit 41 displays the item information 592 in which the order of priority is described in items of contact information on the glasses-type monitor 20 of the user E. In this case, the item information 592 sets the contact information in high priority order as follows: "1: Emergency Car", "2: Medical Office", "3: Security", and "4: Home". In addition, "xxx-xxx" on the drawing means a telephone number of the contact information. In this way, the user E is able to know the contact information in the high priority order, thereby making a phone call for a suitable emergency service without confusing the telephone number of the contact information and the priority order for a call.

In this way, according to the exemplary embodiment of the present invention, the robot safety system 10 includes the distance acquisition unit 43 to acquire respective distances between the robot 11 and a plurality of the users A to E, and the critical distance setting unit 44 to set the critical distance Lx of each of the users A to E on the basis of at least one of the personal information that each of the users A to E individually has and the environment information to be set depending on a setting environment of the robot 11. According to the system configuration described above, the robot safety system 10 is capable of setting the critical distance Lx depending on each of the users A to E.

That is, when a physical fence surrounding the robot 11 is not installed in order for the user and the robot 11 to collaborate with each other, it is required for the user not to approach the robot 11 closer than critical distance Lx so as to prevent the collision, and the like between the user and the robot 11. In this case, when the critical distance Lx is set based on a uniform value regardless of a skill level of the user, a working environment, and work content, the following problems may occur.

For example, in the case of a user whose skill level is high enough to be fully aware of motion of the robot 11, the user may approach the robot 11 at a relatively close distance without causing any problem. In this case, the critical distance Lx is set relatively short, thereby having advantages of not only securing the safety of the highly-skilled worker but also securing the high workability by setting an easy approach to the robot 11. In contrast with the aforementioned highly-skilled worker, setting the critical distance Lx close may result in a possibility of the collision between a low-skilled worker who is not aware of the robot motion and the robot 11, thereby increasing dangerousness therebetween. For this reason, it may be preferable to set the critical distance Lx long to the utmost extent in consideration of the safety of the low-skilled worker. However, when the critical distance Lx is set on the basis of a long range in consideration with the low-skilled worker, it takes more time to approach the robot 11 such that the workability of the highly skilled worker may inversely deteriorate.

Furthermore, a risk degree of work is different depending on environments such as a time period, a working area, and the like. For example, in the case of the time period after a meal time and break, concentration of a user becomes easier to deteriorate such that, as a result, the risk degree of the work becomes easier to be increased. In the case in which the physical fence surrounding the robot 11 is not installed, when the critical distance Lx is set based on the uniform value regardless of the skill level of the user, the working environment, and the work content, a variety of problems may take place in terms of the safety and workability.

According to the exemplary embodiment of the present invention, the critical distance setting unit 44 is capable of setting the critical distance Lx of each of the users A to E with respect to the robot 11 on the basis of at least one of the personal information that each of the users A to E individually has and the environment information to be set depending on the setting environment of the robot 11. Accordingly, the critical distance setting unit 44 is capable of suitably changing and setting the critical distance Lx depending on the skill level of the user, the working environment, and the like. That is, the critical distance Lx is capable of being calculated as a suitable value based on the skill level of each user and the working environment. Consequently, in comparison with the state in which the critical distance Lx is set based on the uniform value, it is possible to accommodate the safety and the workability of the user. Additionally, the robot safety system 10 includes the mounted-type monitor 20 to be respectively mounted on each of the users A to E and to be capable of displaying information thereon within a view of each of the users A to E, and the control unit 41 to control the display content with respect to the glasses-type monitor 20. When the distance between the robot 11 and each of the users A to E becomes less than the critical distance Lx, the control unit 41 shows that the distance between the robot 11 and each of the users A to E becomes less than the critical distance Lx on the glasses-type monitor 20 of each of the users A to E.

Accordingly, information in connection with the safety of each of the users A to E, that is to say, that any one person approaches the robot 11 until the distance therebetween becomes less than the critical distance Lx, is able to be shared among each of the users A to E. Consequently, according to the exemplary embodiment of the present invention, when the user B approaches the robot 11 until the distance therebetween becomes less than the critical distance Lx, for example, the user A, the supervisor, is able to warn the user B to be cautioned, and is able to instruct the user B to switch his or her work with another worker such that the aforementioned countermeasures, and the like are able to be implemented at an early stage. Consequently, in the case of the system in which the robot and the people collaborate with each other, it is accomplished not only to secure the safety of each of the users A to E but also to improve the safety of all of the working regions.

When the distance between the robot 11 and the users A to E becomes less than the critical distance Lx, the control unit 41 is capable of performing a process of at least displaying the user display 54B showing the user B whose distance to the robot 11 becomes less than the critical distance Lx and the user display 54C showing the user C who is closest to the user B whose distance to the robot 11 becomes less than the critical distance Lx on the glasses-type monitor 20 of each of the users A to E with different forms and different colors. Therefore, each of the users A to E easily recognizes any user who has entered the critical region of the robot 11, and any user who is closest to the user who has entered the critical region. In this way, for example, it becomes easier for user A, the supervisor, to instruct the user B who has entered the critical region to switch his or her work with user C who is closest to the user B, thereby securing safety of each of the users A to E in an easier way.

Here, for example, in the case in which the critical distance Lx is set on the basis of the gender, the age, the working experience, and the like of a user such as a worker, and the like, the critical distance Lx suitably fixed for each user is able to be determined to some extent. However, the aforementioned critical distance Lx is able to be adjusted before and after work or in the middle of work, depending on the physical condition of each user on the day he or she works. Here, according to the exemplary embodiment of the present invention, the personal information is configured to include the basic information that is not basically changed during a working process and the biological information that describes information in associated with a living body of each of the users A to E. The basic information, for example, includes the gender, the age, the working experience, and the like of each of the users A to E. The biological information that is able to be changed during the working process, for example, includes the body temperature and the pulse of each of the users A to E. According to the system configuration described above, the critical distance setting unit 44 is capable of setting the critical distance Lx that is suitably adjusted depending on the physical condition of each of the users A to E on the day he or she works. Consequently, the safety of each of the users A to E becomes much easier to be secured, thereby further having an advantage of improving the safety of all of the working regions.

The robot safety system 10 includes the abnormality detection unit 45 to detect the abnormality occurring from each of the users A to E. Furthermore, the control unit 41 is capable of performing a process of displaying the abnormality occurring from the user B on the glasses-type monitors 20 mounted by the users, who are, in this case, the users A and C to E excluding the user B to whom the abnormality has happened. Accordingly, each of the users A and C to E is able to quickly know the abnormality has happened to the user B such that it is possible to promptly take action for rescuing the user B. Consequently, it is possible to improve the safety of each of the users A to E.

The control unit 41 displays the instruction content showing that each of the users, who are, in this case, each of the users A and C to E excluding the user B to whom the abnormality has happened, should take action by individually changing the instruction content for each of the users A and C to E depending on a position of each of the users A and C to E. Accordingly, each of the users A and C to E is able to know what action the user himself or herself should take for the next step without confusion, thereby promptly and efficiently performing a rescue operation for the user B to whom the abnormality has happened.

The control unit 41 displays the user display 57 B showing the user B to whom the abnormality has happened on the mounted-type monitors 20 that other users A, and C to E excluding the user B to whom the abnormality has happened are mounting with the display forms such as different colors that are different from when the abnormality does not occur. According to the system configuration described above, other users A and C to E to whom the abnormality does not happen are able to promptly recognize the user B to whom the abnormality has happened.

Furthermore, the control unit 41 displays the critical distance Lx set to another user, for example, the user C on the mounted-type monitor 20 that the user C is mounting. In this way, the user C who is trying to head for rescuing the user B to whom the abnormality has happened is able to recognize the skill level of the user B by observing whether the user B to whom the abnormality has happened has entered the critical distance Lx set to the user C himself or herself or not. That is, even though the distance between the user B to whom the abnormality has happened and the robot 11 is more distant than the critical distance Lx set to the user C, when a position state of the user B becomes less than the critical distance Lx, it means that the critical distance Lx set to the user B to whom the abnormality has happened is longer than the critical distance Lx set to the user C. In this case, it means that the skill level of the user B to whom the abnormality has happened Is lower than that of the user C. Therefore, another user C to whom the abnormality does not happen is able to promptly determine whether the user B to whom the abnormality currently happens needs urgent support or not due to the lower skill level of the user B than that of the user C by observing the region display 60 of the critical distance of the user C himself or herself that is displayed on the glasses-type monitor 20 to be mounted by the user C himself or herself and the position state of the user B to whom the abnormality has happened.

In addition, according to the system configuration described above, for example, the user C is able to perform the rescue operation for the user B while making sure of the region display 60 showing the critical distance Lx set to the user C himself or herself. Accordingly, for example, in the cases in which the critical distance Lx of the user B is set short due to the high skill level of the user B to whom the abnormality has happened, and on the other hand, the critical distance Lx of the user C is set long due to the low skill level of the user C himself or herself, a factor of the secondary disaster that the user C approaches the robot 11 too closely for rescuing the user B to whom the abnormality has happened is able to be prevented in advance.

Furthermore, it is to be understood that the exemplary embodiments of the present invention are not limited to the disclosed drawings and embodiments, but, on the contrary, are intended to cover various modifications and equivalent arrangements described hereinafter. For example, a laser sensor, a motion detector, and the like detecting a person in each robot 11 may be installed such that it may be configured to specify each position of each of the users A to E based on detection results of the aforementioned sensors, and it may be also configured to specify a position based on an image captured by the imaging unit 22. In addition, it may be configured to specify a relative position with respect to the robot 11 based on the image captured by the imaging unit 22.

The control unit 41 may be respectively installed on the glasses-type monitor 20 that each of the users A to E is mounting.

According to the exemplary embodiment of the present invention, the number of robots 11 and the number of users to be considered as objects herein are not limited. In consideration of the information amount to be displayed on the glasses-type monitor 20 and the possible information amount to be processed by ordinary people, the number of objects with respect to the number of robot 11 and the users may be preferably about 5 units for the robot 11 and about 5 people for the users.

The robot 11 is not limited to be fixed in a specific place. For example, the robot 11 may be also configured as a self-propelled type.

The display unit 21 of the glasses-type monitor 20 is not limited to a transmission display. The display unit 21 of the glasses-type monitor 20, for example, as a non-transmission display type, may also project an image captured by the imaging unit 22 as a view of a user in real time.

Furthermore, a mounted-type monitor is not necessarily required to be the glasses-type monitor 20, and a configuration to be capable of reflecting an image on a display that a worker mounts on the head may be applied thereto.

[Description Of Numerals]

Throughout the drawings, 10 denotes the robot safety system, 20 denotes the glasses-type monitor (mounted-type monitor), 41 denotes the control unit, 43 denotes the distance acquisition unit, 44 denotes the critical distance setting unit, and 45 denotes the abnormality detection unit.

What is claimed is:

1. A robot safety system adapted to be used in a factory in which a plurality of persons work together with an industrial robot, the robot safety system comprising:
   a distance acquisition unit configured to acquire respective distances between the industrial robot and the plurality of persons;
   a critical distance setting unit configured to set a critical distance of each of the persons based on at least one of personal information that each of the persons individually has and environment information to be set depending on a setting environment of the industrial robot;
   a mounted-type monitor configured to be respectively mounted on the plurality of persons and to display information within a view of each of the persons; and
   a control unit configured to control display content with respect to the mounted-type monitor,
   wherein the control unit is configured to perform a process of showing that a distance between the industrial robot and each of the persons becomes less than the critical distance on the mounted-type monitor that each of the persons is mounting, when the distance between the industrial robot and each of the persons becomes less than the critical distance.

2. The robot safety system according to claim 1, wherein the control unit is configured to perform a process of at least displaying a first user display showing a first person whose distance to the industrial robot becomes less than the critical distance and a second user display showing a second person who is closest to the first person whose distance to the industrial robot becomes less than the critical distance on the mounted-type monitor with different forms, when the distance between the industrial robot and the first person becomes less than the critical distance.

3. The robot safety system according to claim 1, wherein the personal information includes basic information that is not basically changed during a working process and biological information that describes information in associated with a living body of the person.

4. The robot safety system according to claim 1,
further comprising an abnormality detection unit configured to detect abnormality occurring from any one person of the plurality of persons or a specific person of the plurality of persons,
wherein the control unit is configured to perform a process of displaying the abnormality occurring from the specific person on the mounted-type monitor mounted by another person excluding the specific person or the plurality of persons.

5. The robot safety system according to claim 4, wherein the control unit is configured to perform a process of displaying instruction content that instructs the another person or each of the plurality of persons of action to take by individually changing the instruction content of each of the persons in accordance with a position of each of the persons.

6. The robot safety system according to claim 4, wherein the control unit is configured to perform a process of displaying a user display showing the specific person on the mounted-type monitor the another person is mounting with a display form that is different from a state in which abnormality is not occurring, and also is configured to perform a process of displaying the critical distance set to the another person on the mounted-type monitor the another person is mounting.

7. The robot safety system according to claim 2, wherein the personal information includes basic information that is not basically changed during a working process and biological information that describes information in associated with a living body of the person.

8. The robot safety system according to claim 7,
further comprising an abnormality detection unit configured to detect abnormality occurring from any one person of the plurality of persons or a specific person of the plurality of persons,
wherein the control unit is configured to perform a process of displaying the abnormality occurring from the specific person on the mounted-type monitor mounted by another person excluding the specific person or the plurality of persons.

9. The robot safety system according to claim 8, wherein the control unit is configured to perform a process of displaying instruction content that instructs the another person or each of the plurality of persons of action to take by individually changing the instruction content of each of the persons in accordance with a position of each of the persons.

10. The robot safety system according to claim 8, wherein the control unit is configured to perform a process of displaying a user display showing the specific person on the mounted-type monitor the another person is mounting with a display form that is different from a state in which abnormality is not occurring, and also is configured to perform a process of displaying the critical distance set to the another person on the mounted-type monitor the another person is mounting.

11. The robot safety system according to claim 3,
further comprising an abnormality detection unit configured to detect abnormality occurring from any one person of the plurality of persons or a specific person of the plurality of persons,
wherein the control unit is configured to perform a process of displaying the abnormality occurring from the specific person on the mounted-type monitor mounted by another person excluding the specific person or the plurality of persons.

12. The robot safety system according to claim 11, wherein the control unit is configured to perform a process of displaying instruction content that instructs the another person or each of the plurality of persons of action to take by individually changing the instruction content of each of the persons in accordance with a position of each of the persons.

13. The robot safety system according to claim 11, wherein the control unit is configured to perform a process of displaying a user display showing the specific person on the mounted-type monitor the another person is mounting with a display form that is different from a state in which abnormality is not occurring, and also is configured to perform a process of displaying the critical distance set to the another person on the mounted-type monitor the another person is mounting.

* * * * *